(12) United States Patent
Messersmith et al.

(10) Patent No.: US 10,307,415 B2
(45) Date of Patent: Jun. 4, 2019

(54) EPIMORPHIC REGENERATION AND RELATED HYDROGEL DELIVERY SYSTEMS

(71) Applicants: Northwestern University, Evanston, IL (US); The Wistar Institute of Anatomy and Biology, Philadelphia, PA (US)

(72) Inventors: Phillip B. Messersmith, Clarendon Hills, IL (US); Iossif A. Strehin, Lincolnshire, IL (US); Ellen Heber-Katz, Philadelphia, PA (US)

(73) Assignees: Northwestern University, Evanston, IL (US); The Wistar Institute of Anatomy and Biology, Philadelphia, PA (US)

( * ) Notice: Subject to any disclaimer, the term of this patent is extended or adjusted under 35 U.S.C. 154(b) by 0 days.

(21) Appl. No.: 15/618,715

(22) Filed: Jun. 9, 2017

(65) Prior Publication Data
US 2017/0273971 A1 Sep. 28, 2017

Related U.S. Application Data

(62) Division of application No. 14/544,003, filed on Nov. 13, 2014, now Pat. No. 9,675,607.
(Continued)

(51) Int. Cl.
*A61K 31/4745* (2006.01)
*C12N 9/02* (2006.01)
(Continued)

(52) U.S. Cl.
CPC .......... *A61K 31/4745* (2013.01); *A61K 47/60* (2017.08); *C08G 65/332* (2013.01); *C08G 65/333* (2013.01); *C08G 65/3342* (2013.01); *C08G 65/3344* (2013.01); *C08G 65/3348* (2013.01); *C08G 65/33331* (2013.01);
(Continued)

(58) Field of Classification Search
CPC .......... A61K 47/48215; A61K 31/4745; C08G 65/33396
See application file for complete search history.

(56) References Cited

U.S. PATENT DOCUMENTS 5,681,964 A * 10/1997 Ashton ................ C07D 209/26
548/491
2005/0181023 A1* 8/2005 Young .................. A61K 9/1647
424/443

(Continued)

OTHER PUBLICATIONS

Tan, M. et al., "SAG/ROC2/RBX2 is a HIF-1 target gene that promotes HIF-1 alpha ubiquitination and degradation", Oncogene 27, 1404-1411 (2008).
(Continued)

*Primary Examiner* — Jianfeng Song
(74) *Attorney, Agent, or Firm* — Reinhart Boerner Van Deuren s.c.

(57) ABSTRACT

Methods and compositions are described for enhancing tissue regeneration or wound repair in a mammalian subject comprising a composition comprising (a) a proline hydroxylase inhibitor component or molecule that increases or upregulates HIF1a and (b) a carrier component comprising a hydrogel.

4 Claims, 15 Drawing Sheets
(13 of 15 Drawing Sheet(s) Filed in Color)

Related U.S. Application Data

(60) Provisional application No. 61/962,637, filed on Nov. 13, 2013.

(51) Int. Cl.
  *C08G 65/333* (2006.01)
  *C08G 65/332* (2006.01)
  *C08G 65/334* (2006.01)
  *A61K 47/60* (2017.01)

(52) U.S. Cl.
  CPC . *C08G 65/33337* (2013.01); *C08G 65/33396* (2013.01); *C12N 9/0071* (2013.01); *C08G 2210/00* (2013.01); *C08G 2650/32* (2013.01); *C08G 2650/58* (2013.01); *C08L 2203/02* (2013.01); *C12Y 114/11002* (2013.01)

(56) References Cited

U.S. PATENT DOCUMENTS

2011/0262492 A1* 10/2011 Messersmith ........ C07D 333/36
  424/400
2011/0293669 A1* 12/2011 Bennett .................... A61K 9/06
  424/400
2012/0156259 A1* 6/2012 Rau ....................... A61K 9/0024
  424/400

OTHER PUBLICATIONS

Wenger, R.H. et al., "Integration of oxygen signaling at the consensus", HRE. Sci. STKE 2005, re12 (2005).
Zhang, X.J. et al., "Importance of hypoxia-inducible factor 1 alpha in the healing of burn wounds in murine model", Wound Repair Regen. 17, A87-A87 (2009).
Franklin, T.J. et al., "Inhibition of prolyl 4-hydroxylase in vitro and in vivo by members of a novel series of phenanthrolinones" Biochem. J. 353, 333-338 (2001).
Kim, I. et al., "Inhibition of prolyl 4 hydroxylase reduces scar hypertrophy in a rabbit model of cutaneous scarring", Wound Repair Regen. 11, 368-372 (2003).
Botusan, I. R., et al., "Stabilization of HIF-1 alpha is critical to improve wound healing in diabetic mice", Proc. Natl. Acad. Sci. U.S.A. 105, 19426-19431 (2008).
Strehin, I. et al, "Hydrogels Formed by Oxo-ester Mediated Native Chemical Ligation", Biomater. Sci., 2013, 1, 603-613.
Ni, P. et al., "Preparation of poly(ethylene glycol)/polylactide hybrid fibrous scaffolds for bone tissue engineering", 2011 Internat. J Nanomedicine, 6, 3065-3075.
U.S. Appl. No. 14/544,003, filed Nov. 13, 2014.

* cited by examiner

Figure 1A
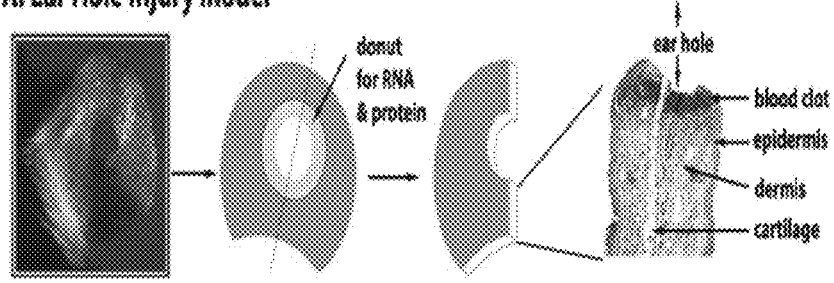
Figure 1B
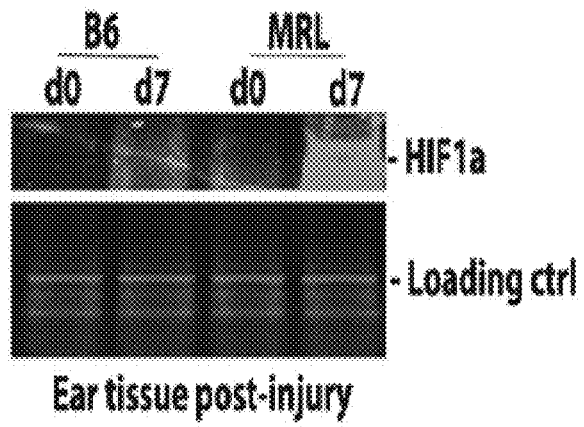
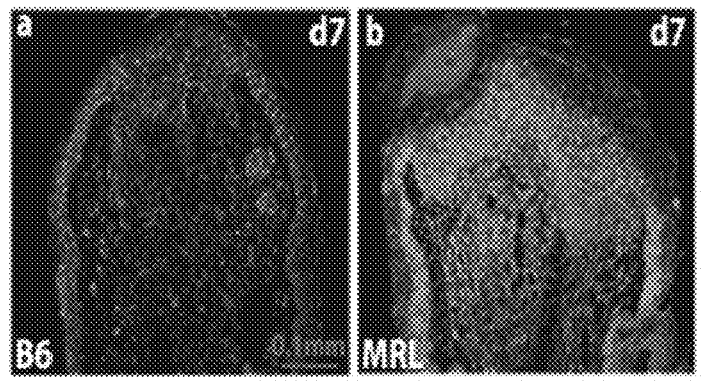
Fig. 1Ca            Fig. 1Cb

Figure 1D
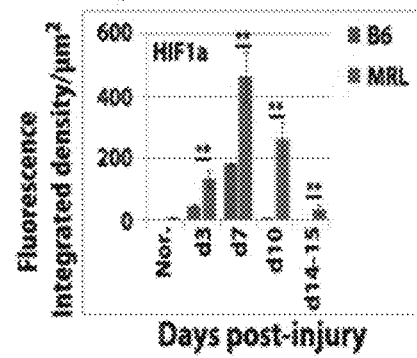
E. Bioluminescence Post-injury
| a  B6 cross | b  MRL cross | c  B6 cross | d  MRL cross |
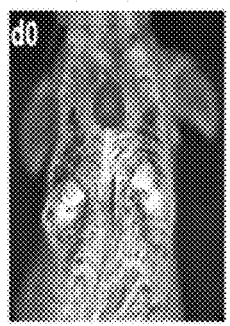 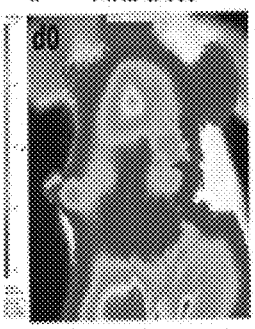 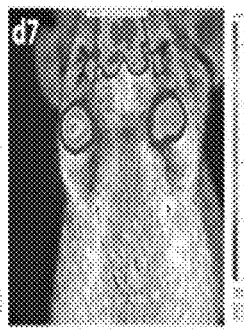 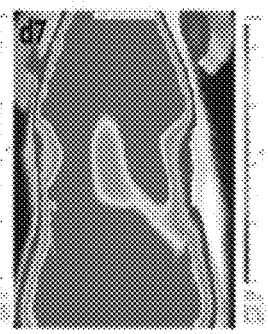
Fig. 1Ea  Fig. 1Eb  Fig. 1Ec  Fig. 1Ed
Figure 1F
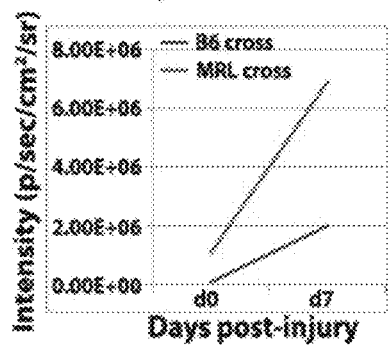

Figure 1G
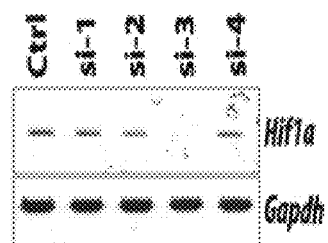
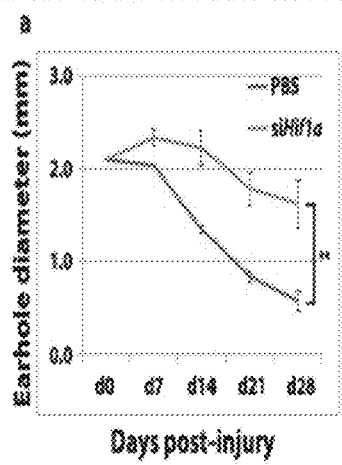
Fig. 1Ha
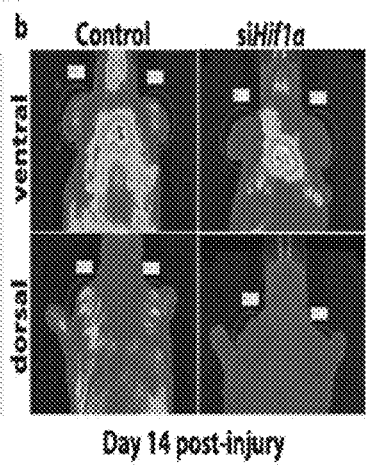
Fig. 1Hb
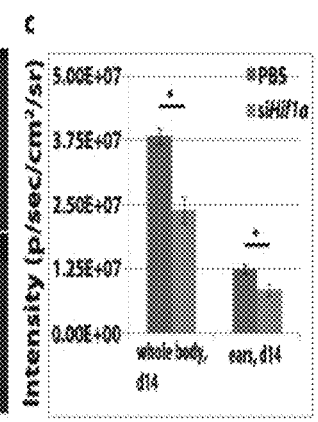
Fig. 1Hc

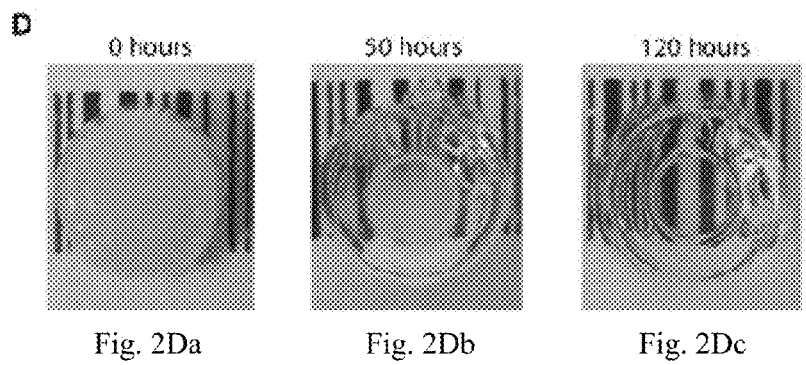
Fig. 2Da  Fig. 2Db  Fig. 2Dc
Figure 2E
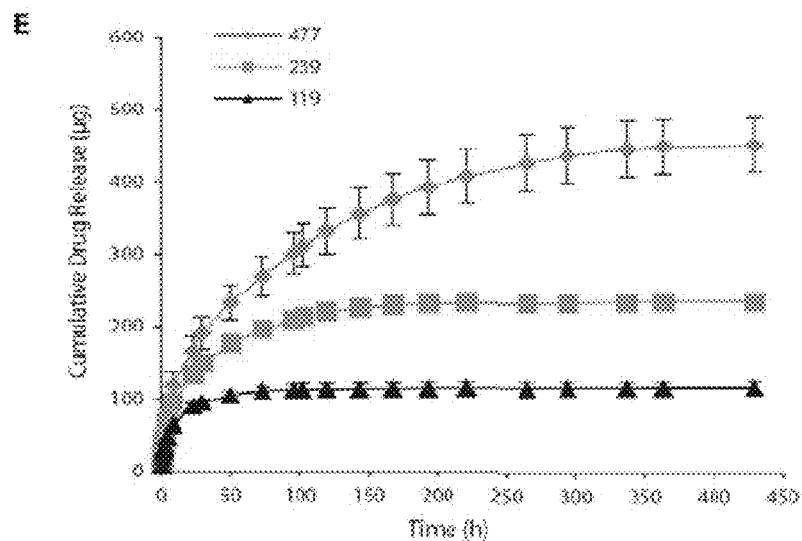

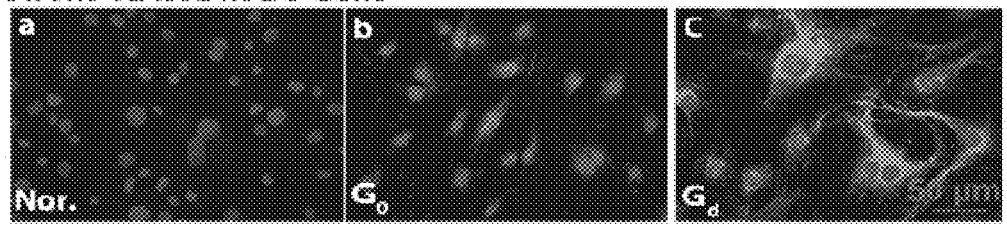
Fig. 3Aa    Fig. 3Ab    Fig. 3Ac
Figure 3B
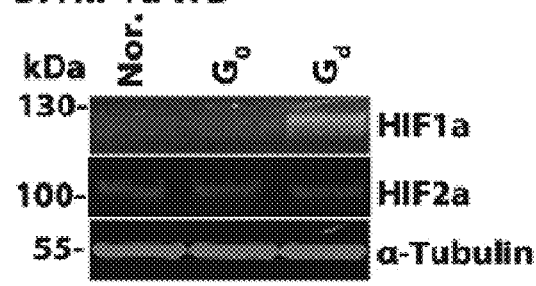
Figure 3C
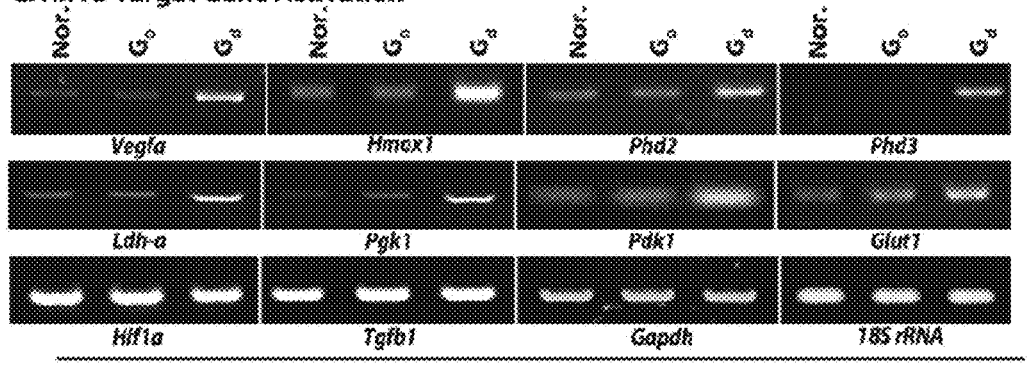

Figure 3D
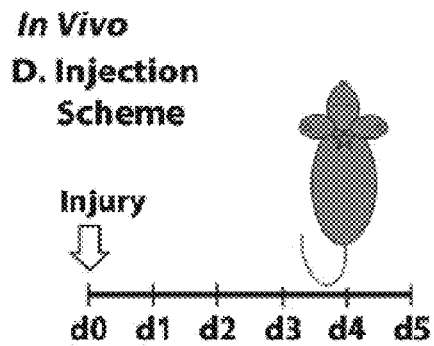
Figure 3E
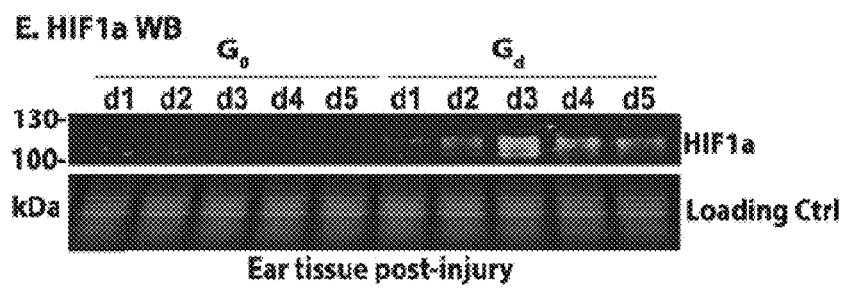
F. HIF1a IHC in Ear Tissue    Fig. 3Fb
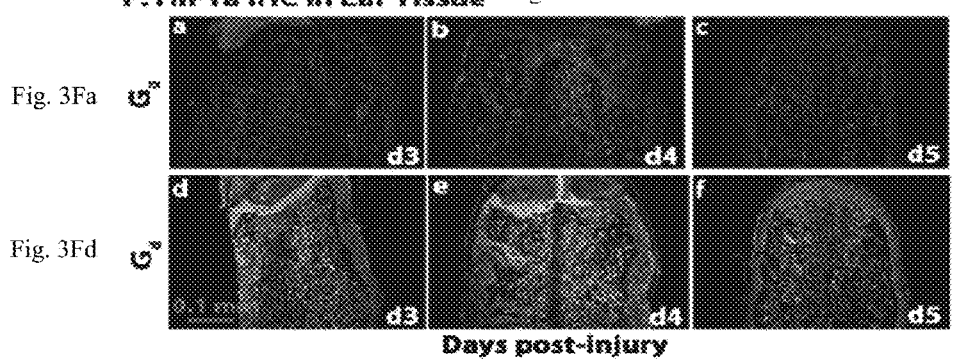
Fig. 3Fa      Fig. 3Fc
Fig. 3Fd      Fig. 3Ff
Fig. 3Fe Figure 4A
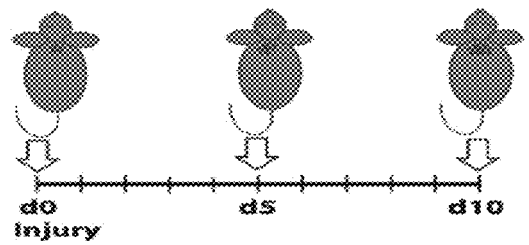
Fig. 4Ba
Fig. 4Bb
Fig. 4Bc
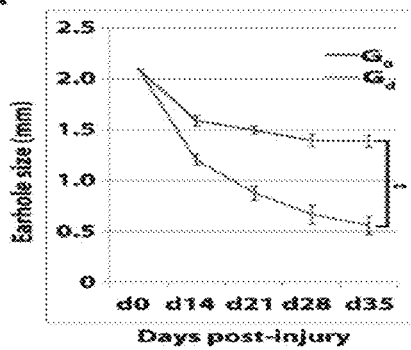
Fig. 4Bd
Fig. 4Ca
Fig. 4Cb
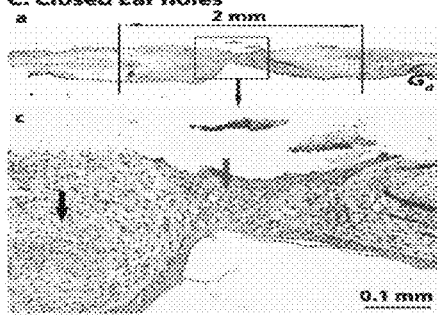
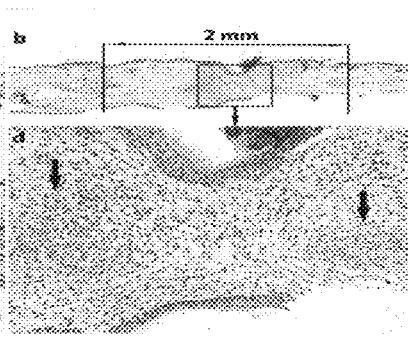
Fig. 4Cc
Fig. 4Cd

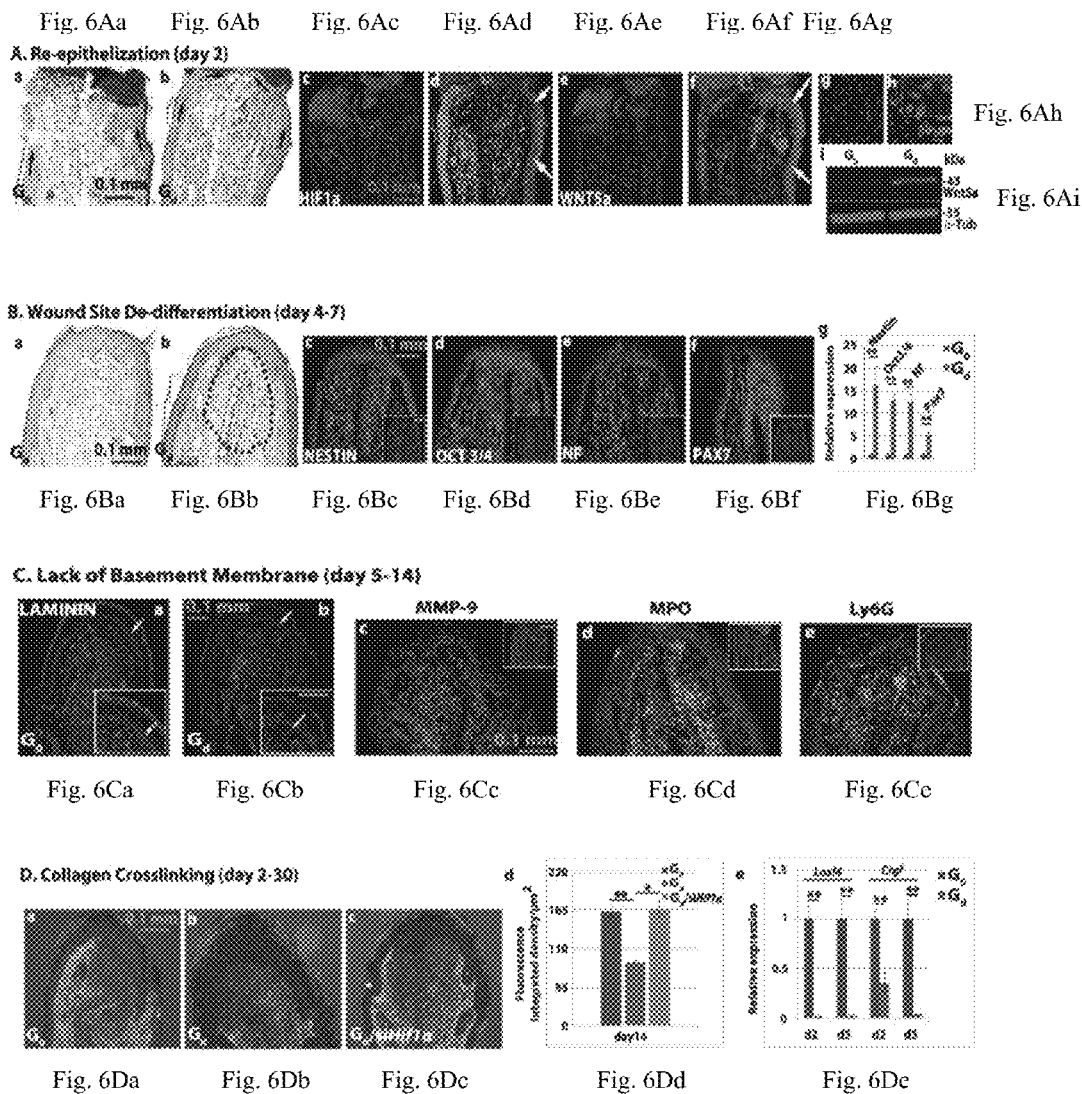

EPIMORPHIC REGENERATION AND RELATED HYDROGEL DELIVERY SYSTEMS

This application is a divisional of and claims priority to and the benefit of application Ser. No. 14/544,003 filed Nov. 13, 2014 and issued as U.S. Pat. No. 9,675,607 on Jun. 13, 2017, which claimed priority to and the benefit of application Ser. No. 61/962,637 filed Nov. 13, 2013—each of which is incorporated herein by reference in its entirety.

This invention was made with government support under RO1 DE021215, DE021104 and P30 CA010815 awarded by the National Institutes of Health. The government has certain rights in the invention.

BACKGROUND OF THE INVENTION

Wound repair and regeneration are two separable biological processes by which organisms heal wounds. As a model of regeneration in mammals, ear hole closure, as seen in rabbits, in the inbred mouse strains MRL/MpJ and LG/J and other mutant mouse strains shows multiple similarities to limb regeneration in amphibians including the replacement of cartilage and the lack of scarring. Other less well known classical regenerative phenotypes are also seen in the MRL ear injury model include rapid re-epithelialization, enhanced tissue remodeling, basement membrane breakdown, blastema growth and re-differentiation not seen during wound repair. Inflammation is now considered a factor in regenerative processes and its role in ear hole closure has been further demonstrated in genetically selected, pro-inflammatory AIR (acute inflammatory reactivity) mice which have the ability to close ear holes. Another aspect of adult MRL mice is the use of aerobic glycolysis for normal metabolism, which may contribute to the regenerative response. This metabolic state contributes to inflammation, with glycolysis playing an important role in migration and activity of inflammatory cells. The molecule hypoxia inducible factor (HIF1a) is a central node in all of these and could potentially be a main actor in the MRL ear hole closure response.

HIF1a is an oxygen-regulated protein which functions as part of a heterodimeric complex formed with HIF1b in the nucleus and binds to DNA at specific promoter or enhancer sites (i.e., HREs or hypoxia response elements), thereby regulating the transcription of over 100 gene products. These include molecules of interest in regenerative processes involved in 1) angiogenesis through the induction of VEGF, VEGFR-1, and PDGF and erythropoietin (EPO); 2) tissue remodeling with the induction of uPAR, MMP2 and 9 and TIMPs; and 3) glycolytic metabolism with the induction of lactate dehydrogenase (LDH) which converts pyruvate into lactate and of pyruvate dehydrogenase kinase (PDK) which blocks pyruvate's entry into the TCA cycle. HIF1a protein is generally short-lived in the cytoplasm because under normoxic conditions, it is continually being hydroxylated by prolyl hydroxylases (PHDs), then bound by the von Hippel-Lindau tumor suppressor protein (pVHL) and the more recently identified SAG/ROC/RBX2 E3 ubiquitin ligase complex which targets the molecule for proteolysis. (M. Tan, Q. Gu, H. He, D. Pamarthy, G. L. Semenza, Y. Sun, SAG/ROC2/RBX2 is a HIF-1 target gene that promotes HIF-1 alpha ubiquitination and degradation. *Oncogene* 27, 1404-1411 (2008).) In low oxygen, hydroxylation is inhibited and HIF1a protein survives and is translocated to the nucleus where it binds HIF1b and can now function as a transcription factor, binding to the appropriate DNA elements or HRE. (R. H. Wenger, D. P. Stiehl, G. Camenisch, Integration of oxygen signaling at the consensus HRE. *Sci. STKE* 2005, re12 (2005).)

The stabilization of HIF1a protein has been accomplished through the inhibition of PHDs, molecules actively involved in collagen secretion and crosslinking. PHDs control collagen deposition in fibrosis, response to ischemia, and wound repair. (See, e.g., X. J. Zhang, L. X. Liu, X. F. Wei, Y. S. Tan, L. Tong, R. Chang, G. Marti, M. Reinblatt, J. W. Harmon, G. L. Semenza, Importance of hypoxia-inducible factor 1 alpha in the healing of burn wounds in murine model. *Wound Repair Regen.* 17, A87-A87 (2009); T. J. Franklin, W. P. Morris, P. N. Edwards, M. S. Large, R. Stephenson, Inhibition of prolyl 4-hydroxylase in vitro and in vivo by members of a novel series of phenanthrolinones. *Biochem. J.* 353, 333-338 (2001); I. Kim, J. E. Mogford, C. Witschi, M. Nafissi, T. A. Mustoe, Inhibition of prolyl 4-hydroxylase reduces scar hypertrophy in a rabbit model of cutaneous scarring. *Wound Repair Regen.* 11, 368-372 (2003).) Considering the impact of scar formation on regeneration, inhibition of PHDs could have a two-fold effect; the up-regulation of HIF1a and the down-regulation of scarring. In a chronic diabetic wound model, the use of PHD-inhibiting compounds applied locally to a wound can accelerate wound repair in the presence of increased vascularity and granulation tissue. (I. R. Botusan, V. G. Sunkari, O. Savu, A. I. Catrina, J. Grunler, S. Lindberg, T. Pereira, S. Yla-Herttuala, L. Poellinger, K. Brismar, S. B. Catrina, Stabilization of HIF-1 alpha is critical to improve wound healing in diabetic mice. *Proc. Natl. Acad. Sci. U.S.A.* 105, 19426-19431 (2008).)

However, the effectiveness of various PHD inhibitor compounds can be compromised by low solubility under physiological conditions, inefficient routes of administration and/or untimely delivery of therapeutic dose levels. There remains an on-going concern in the art to provide a delivery system and methodology to better utilize the benefits and advantages available through such inhibitor compounds.

SUMMARY OF THE INVENTION

In light of the foregoing, it can be an object of the present invention to provide one or more methods for epimorphic regeneration and/or related hydrogel delivery systems, thereby overcoming various deficiencies and shortcomings of the prior art, including those outlined above.

Other objects, features, benefits and advantages of the present invention from this summary and the following descriptions of certain embodiments, and will be readily apparent to those skilled in the art having knowledge of various hydrogel drug delivery systems and methods for tissue regeneration. Such objects, features, benefits and advantages will be apparent from the above as taken into conjunction with the accompanying examples, data, figures and all reasonable inferences to be drawn therefrom, alone or with consideration of the reference(s) enclosed herein.

In one aspect, a method of tissue regeneration or epimorphic regeneration is disclosed which comprises providing a composition comprising (a) a molecule that increases or upregulates HIF1a, such as a proline hydroxylase inhibitor component and (b) a pharmaceutically acceptable carrier component, such as a carrier comprising a hydrogel.

Without limitation, in certain embodiments, component (a) of the composition being administered can include an inhibitor which is a prodrug of 1,4-DPCA or 1,4-dihydrophenonthrolin-4-one-3-carboxylic acid, or a salt thereof. 1,4-DPCA is a selective and potent inhibitor of prolyl 4-hydroxylase and has been shown to potently increase cellular HIF1a protein levels. 1,4-DPCA is registered as CAS 331830-20-7; has a molecular weight of 240.2 and a molecular formula of $C_{13}H_8N_2O_3$. The structure of 1,4 DPCA is

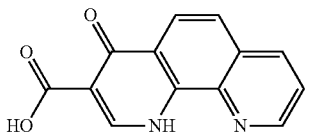 [SMILES: O=C(O)c1c[nH]c2c(ccc3cccnc32)c1=O]

The drug 1,4-DPCA is publically available from a number of sources, e.g., Cayman Chemical, Enzo Life Sciences, etc.

In another embodiment, such a prodrug can comprise a poly(ethylene oxide) component. In certain such embodiments, such a component can be a poly(alkylene oxide) block copolymer. In another embodiment, additional molecules are anticipated to work in the compositions described herein in a manner similar to the exemplified 1,4-DPCA. Still other small molecules or drugs that increase or upregulate HIF1a are anticipated to be similarly useful in the compositions and methods described herein.

In another embodiment, the molecule or drug that increases or upregulates HIF1a is DMOG or dimethyloxallyl glycine, or a salt thereof. DMOG is registered as CAS 89464-63-1, has a molecular weight of 175.1 and a molecular formula of $C_6H_9NO_5$. The structure of DMOG is

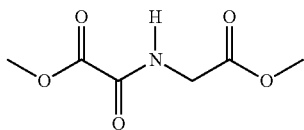

The drug DMOG is publically available from a number of sources, e.g., Cayman Chemical, Enzo Life Sciences, etc.

In another embodiment, the molecule or drug that increases or upregulates HIF1a is DFX or desferrioxamine B, also known as 30-amino-3,14,25-trihydroxy-3,9,14,20,25-pentaazatriacontane-2,10,13,21,24-pentone, or a salt thereof. DFX is registered as CAS 70-51-9; has the formula $C_{25}H_{48}N_6O_8$ and a molecular weight of 560.68. The drug DFX is publically available from a number of sources, e.g., Sigma Chemical.

In another embodiment, the molecule or drug that increases or upregulates HIF1a is 1-(2-methylpropyl)-1H-imidazo[4,5-c]quinolin-4-amine or Imiquimod, or a salt thereof. Imiquimod has a molecular formula of $C_{14}H_{16}N_4$ and a molecular weight of 240.3. Its structural formula is:

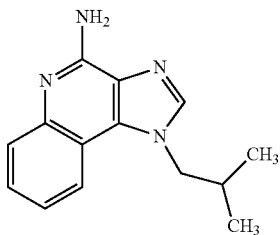 [SMILES: CC(C)Cn1cnc2c(N)nc3ccccc3c21]

The drug Imiquimod is publically available from a number of sources.

In another embodiment, the molecule or drug that increases or upregulates HIF1a is cobalt II chloride or $CoCl_2$. $CoCl_2$ is available from a number of sources, e.g., Sigma-Aldrich. These additional molecules are anticipated to work in the compositions described herein in a manner similar to the exemplified 1,4-DPCA. Still other small molecules or drugs that increase or upregulate HIF1a are anticipated to be similarly useful in the compositions and methods described herein.

In another aspect, a method for enhancing tissue regeneration or wound repair in a mammalian subject, comprises administering to the subject in need thereof a composition comprising a molecule that up-regulates HIF1a in a pharmaceutically acceptable carrier. In one embodiment, the composition comprises (a) a proline hydroxylase inhibitor component or molecule that increases or upregulates HIF1a; and (b) a carrier component comprising a hydrogel. In another embodiment, the composition employs as the upregulating HIF1a molecule 1, 4-DPCA, DMOG, DFX, Imiquimod or $CoCl_2$. In certain embodiments, the administration involves contacting a cellular medium with the composition. In another embodiment, the method comprises systemically administering to a subject in need thereof the composition described herein. In another embodiment, the method comprises administering the composition to a mammalian subject in need thereof at a site distal from the site of a wound or injury. In another embodiment, the method comprises administering the composition to a mammalian subject in need thereof at a site local or adjacent to the site of a wound or injury.

In another embodiment, the method further comprises administering the composition at a drug release rate which achieves maximal HIF1a upregulation in vitro. In another embodiment, the method involves administering the composition and releasing the HIF1a up-regulator at a continuous rate over at least 4 days.

In part, the present invention can be directed to a method of epimorphic regeneration. Such a method can comprise providing a composition comprising a proline hydroxylase inhibitor component and a carrier component comprising a hydrogel comprising a condensation product of

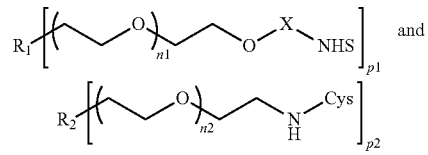

wherein $R_1$ and $R_2$ can be independently selected from polyhydric core moieties; X can be selected from divalent linker moieties; n1 and n2 can be integers from 1 to about 201; p1 and p2 can be integers independently selected from 2 to about 10, corresponding to the polyol from which $R_1$ and $R_2$ are derived; NHS can be a N-hydroxysuccinimido moiety; and Cys can be an N-terminal cysteine residue; and contacting such a proline hydroxylase inhibitor component with a cellular medium expressing a proline hydroxylase, such a component as can be in an amount over a time at least partially sufficient to produce a regenerative response. Without limitation, such a regenerative response can be considered in the context of a functional effect achieved therewith, such a functional effect including but not limited to enhanced tissue remodeling response, de-differentiated cellular signature, increased glycolytic enzymes, increased components of inflammatory response and increased angiogenesis. In certain embodiments, such a cellular medium can be within a non-regenerative mammal presenting a tissue injury. In certain such embodiments, such a composition can be administered distal to such an injury. Without limitation, administration can comprise subcutaneous injection and, with respect to certain such embodiments, multiple injections over time.

Regardless, with respect to certain embodiments, $R_1$ and $R_2$ can be independently selected from hexaglycolic and tripentaerythritolic moieties, such that each of p1 and p2 can be 8. In certain such embodiments, X can be a $C_4$-$C_6$ dicarbonyl moiety. In certain such embodiments, X can be selected from $C(O)(CH_2)_3(CO)$, $C(O)CH_2OCH_2C(O)$, $C(O)CH_2CH(CH_3)CH_2C(O)$, $C(O)(CH_2)_2C(O)$ and $C(O)CH_2CH(CH_3)C(O)$ moieties. Without limitation, in certain embodiments, such an inhibitor component can comprise a prodrug of 1,4-DPCA. In certain such embodiments, such a prodrug can comprise a poly(ethylene oxide) component. In certain such embodiments, such a component can be a poly(alkylene oxide) block copolymer.

In one embodiment, a carrier is a hydrogel delivery system comprising a derivatized polyethylene glycol (PEG) that crosslinks in situ via oxoester mediated native chemical ligation. One such hydrogel delivery system comprises a derivatized polyethylene glycol (PEG) that crosslinks in situ via oxoester mediated native chemical ligation. The hydrogel can comprise a derivatized PEG, such as PEG-Cys8 (P8Cys) or PEG-NHS8 (P8NHS), and be prepared as described in detail in Strehin et al, 2013, *Biomater. Sci.*, 2013, 1, 603-613 incorporated by reference herein.

In yet further embodiments, the term "pharmaceutically acceptable carrier" can include a biologically compatible fluid medium, solution or pharmaceutically acceptable delivery vehicle suitable for the form of the composition. The various components of the composition may be prepared for administration by being suspended, dispersed or dissolved in a pharmaceutically or physiologically acceptable carrier such as isotonic saline; isotonic salts solution or other formulations that will be apparent to those skilled in such administration. Other aqueous and non-aqueous isotonic sterile injection solutions and aqueous and non-aqueous sterile suspensions known to be pharmaceutically acceptable carriers and well known to those of skill in the art may be employed for this purpose. As used herein the term "pharmaceutically acceptable carrier" or "diluent" is intended to further include any and all solvents, dispersion media, coatings, antibacterial and antifungal agents, isotonic and absorption delaying agents, and the like, compatible with administration to humans. In one embodiment, the diluent is saline or buffered saline.

Still other examples of carrier materials suitable for systemic, distal, or local administration of the composition comprising the HIF1a-increasing or up-regulating composition may be selected by one of skill in the art, such as biomaterials admixed with the HIF-1a inducing composition, which are able to be implanted in the site of the wound. An example of such a material are those described in, e.g., Ni, et al, 2011 *Internat. J Nanomedicine*, 6:3065-3075.

In one embodiment, the use of a hydrogel system to deliver 1,4-DPCA permits the drug to be released at a rate that achieves a reliable and predictable steady state of drug concentration in vivo. This controlled release of a composition that achieves a maximal HIF1a upregulation in vitro increases HIF1a, while decreasing the toxicity or side effects that may be observed in upon other modes of delivery of the molecule. Regenerative effects of the use of certain embodiments of these compositions are described in detail below and in the examples.

The method of tissue regeneration or epimorphic regeneration also comprises contacting such a composition containing component (a) and (b) with, or administering the composition into, a cellular medium. In one embodiment, the medium expresses a proline hydroxylase.

By "cellular medium" as used herein is meant an ex vivo sample containing mammalian cells or an in vivo tissue or mammalian cells, e.g., in a mammalian subject. In certain embodiments, such a cellular medium containing mammalian cells can be an in vitro sample containing cells, such as a sample of cells removed from a mammalian subject, cultured ex vivo, and contacted ex vivo with the compositions as described herein. Such an ex vivo-contacted cellular medium is then itself transferred or reimplanted to the site of cellular or tissue injury in the mammalian subject. In another embodiment, the cellular mediam refer to cells or tissue within a mammal presenting a tissue injury, so that the contacting step involves in vivo administration to the mammalian subject of the composition described herein. A mammalian subject includes a human, a veterinary or farm animal, a domestic animal or pet, rodents and animals normally used as mammalian models for clinical research, such as the mouse models described in the examples.

For use in the contacting step, the proline hydroxylase inhibitor/HIF1a increasing drug component is present in the composition in an amount that is at least partially sufficient to produce a regenerative response in the cells of the cellular medium. The contacting step can occur for a time at least partially sufficient to produce a regenerative response. Without limitation, a regenerative response can be defined as the functional effect achieved by contact between the cells of the sample and the composition. Such a functional effect includes but is not limited to enhanced tissue remodeling response, de-differentiated cellular signature, increased glycolytic enzymes, increased components of inflammatory response and increased angiogenesis.

In one embodiment, the methods of this invention comprise systemically administering the composition to a subject in need thereof. In another embodiment, the methods described herein involve administering to a subject in need thereof the composition at a site distal to the cells or tissue to be regenerated, e.g., distal to the wound. In another embodiment, the methods described herein involve locally administering at or near the site of the wound in a subject in need thereof the composition in an amount that permits sufficient HIF1a upregulation to induce wound healing or tissue repair with minimal toxicity to the subject. In one embodiment, the composition is administered at a drug release rate which achieves maximal HIF1a upregulation when assayed in vitro. In one embodiment, the concentration of the HIF1a-upregulating molecule is kept at a concentration low enough to avoid toxic side effects.

In another embodiment, the composition releases the HIF1a up-regulator at a continuous, non-toxic rate over at least 1 or more days, at least one week, at least two weeks, or more than 3 weeks. In certain embodiments, the composition is administered for at least one week, or at least 4 weeks at a desired concentration level to enhance the pace of wound healing. The level of administration may be selected or adjusted based upon the nature and site of the wound or tissue being regenerated.

The method may be accomplished by administering the appropriate construct or composition by a suitable route. In one embodiment of the methods, the compositions are administered directly into the subject or into the subject's tissue requiring repair or regeneration, where possible. Conventional and pharmaceutically acceptable routes of administration include, but are not limited to, systemic routes, such as oral intake and subcutaneous administration. In one embodiment, such a composition can be administered distal to such an injury. Without limitation, administration can comprise subcutaneous injection. Other routes of administration may include intraperitoneal, intravenous, intranasal, intravenous, intramuscular, intratracheal, topical, and other parenteral routes of administration. Routes of administration may be combined, if desired. In some embodiments, the administration is repeated periodically by multiple doses and/or injections over time.

Dosages of these therapeutic compositions employed in these methods will depend primarily on factors such as the tissue or injury being treated, the age, weight and health of the patient, and may thus vary among patients. Methods for determining the timing of frequency of administration or use of continuous release will include an assessment of tissue response.

In another embodiment, the method further comprises administering to the subject along with the therapeutic compositions that increase or up-regulate HIF1a, an adjunctive therapy directed toward the tissue being treated.

In another aspect, a method of tissue regeneration or epimorphic regeneration is disclosed which comprises providing a composition comprising (a) a molecule or drug that increases or upregulates HIF1a and (b) a carrier component comprising a hydrogel as described above.

In one aspect, the proline hydroxylase inhibitor molecule or drug that increases or upregulates HIF1a is 1, 4-DPCA or 1,4-dihydrophenonthrolin-4-one-3-carboxylic acid, or a salt thereof. 1,4-DPCA is a selective and potent inhibitor of prolyl 4-hydroxylase and has been shown by others to potently increase cellular HIF1a protein levels. 1,4-DPCA is registered as CAS 331830-20-7; has a molecular weight of 240.2 and a molecular formula of $C_{13}H_8N_2O_3$. The structure of 1,4 DPCA is

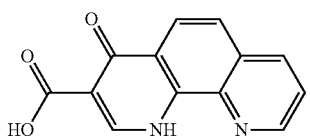 [SMILES: O=C(O)c1c[nH]c2c(ccc3cccnc32)c1=O]

The drug 1, 4-DPCA is publically available from a number of sources, e.g., Cayman Chemical, Enzo Life Sciences, etc.

In another embodiment, the molecule or drug that increases or upregulates HIF1a is DMOG or dimethyloxallyl glycine, or a salt thereof. DMOG is registered as CAS 89464-63-1 and has a molecular weight of 175.1 and a molecular formula of $C_6H_9NO_5$. The structure of DMOG is

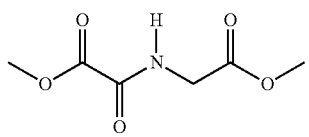

The drug DMOG is publically available from a number of sources, e.g., Cayman Chemical, Enzo Life Sciences, etc.

In another embodiment, the molecule or drug that increases or upregulates HIF1a is DFX or desferrioxamine B, also known as 30-amino-3,14,25-trihydroxy-3,9,14,20,25-pentaazatriacontane-2,10,13,21,24-pentone, or a salt thereof. DFX is registered as CAS 70-51-9; has the formula $C_{25}H_{48}N_6O_8$ and a molecular weight of 560.68. The drug DFX is publically available from a number of sources, e.g., Sigma Chemical.

In another embodiment, the molecule or drug that increases or upregulates HIF1a is 1-(2-methylpropyl)-1H-imidazo[4,5-c]quinolin-4-amine or Imiquimod, or a salt thereof. Imiquimod has a molecular formula of $C_{14}H_{16}N_4$ and a molecular weight of 240.3. Its structural formula is:

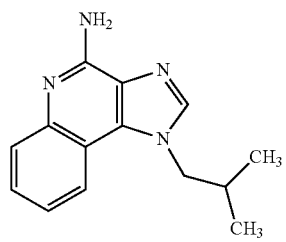 [SMILES: CC(C)Cn1cnc2c(N)nc3ccccc3c21]

The drug Imiquimod is publically available from a number of sources.

In another embodiment, the molecule or drug that increases or upregulates HIF1a is cobalt II chloride or $CoCl_2$. $CoCl_2$ is available from a number of sources, e.g., Sigma-Aldrich.

Without limitation, in certain embodiments, such an inhibitor component can comprise a prodrug of 1,4-DPCA. In certain such embodiments, such a prodrug can comprise a poly(ethylene oxide) component. In certain such embodiments, such a component can be a poly(alkylene oxide) block copolymer.

In part, the present invention can also be directed toward a method of modulating proline hydroxylase activity. Such a method can comprise providing a composition comprising a prodrug of 1,4-DPCA and a carrier component comprising a hydrogel comprising a chemical ligation product of

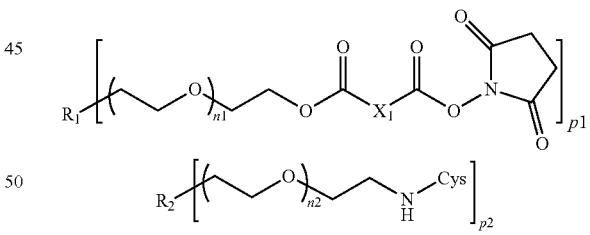

wherein $R_1$ and $R_2$ can be independently selected from polyhydric core moieties of the sort described herein; $X_1$ can be selected from divalent $(CH_2)_3$, $CH_2OCH_2$, $CH_2CH(CH_3)$ $CH_2$, $(CH_2)_2$, and $CH_2CH(CH_3)$ moieties; and n1, n2, p1 and p2 can be as described elsewhere herein; and contacting such a 1,4-DPCA component of such a prodrug with a cellular medium expressing a proline hydroxylase, such a component as can be in an amount at least partially sufficient to modulate, inhibit or otherwise affect proline hydroxylase activity in such a cellular medium. Without limitation, such a cellular medium can be within a non-regenerative mammal presenting a tissue injury.

In certain embodiments, such administration can be distal to an injury. Without limitation, administration can be by subcutaneous, intraperitoneal and/or intramuscular injection and, with respect to certain such embodiments, can comprise multiple injections over time to stabilize a constitutive cellular level of HIF1a protein. Regardless, in certain embodiments, each of $R_1$ and $R_2$ can be a hexaglycolic moiety, such that each of p1 and p2 can be 8, and X can be a $(CH_2)_3$ moiety. Without limitation, 1,4-DPCA can be coupled to a poly(alkylene oxide) block copolymer.

In part, the present invention can be directed to a drug delivery system. Such a system can comprise a first macromonomer component comprising a first reactive moiety; a second macromonomer component comprising a second reactive moiety reactive with such a first reactive moiety; and a drug component selected from proline hydroxylase inhibitor compounds and prodrugs thereof. Without limitation, such a prodrug can comprise such a proline hydroxylase inhibitor compound coupled to a cleavable polymer component. In certain embodiments, each such macromonomer component can be in a fluid medium. In certain other embodiments, upon contact one with the other, such first and second macromonomer components can be cross-linked to provide a hydrogel, and such a drug component can be suspended or dispersed therein. Regardless, such a drug component can be selected from 1,4-DPCA, a poly(alkylene oxide) coupled prodrug of 1,4-DPCA, DMOG, DFX, Imiquimod and $CoCl_2$ or other proline hydroxylase inhibitor compounds as would be understood by those skilled in the art. Likewise, such a drug delivery system would be understood by those skilled in the art made aware of this invention, such delivery systems, comprising first and second macromonomer components, as are described in co-pending application Ser. No. 13/798,744 filed Mar. 13, 2013, incorporated herein by reference in its entirety and as discussed more fully below. Accordingly, with respect to such a drug delivery system, a first reactive moiety of such a first macromonomer component can be an N-hydroxysuccinimide ester moiety, and a second reactive moiety of such a second macromonomer component can be an N-terminal cysteine moiety.

In part, the present invention can also be directed toward a method of using a hydrogel system to modulate cellular levels of HIF1a protein. Such a method can comprise providing a first hydrogel precursor component comprising a fluid and/or aqueous medium comprising

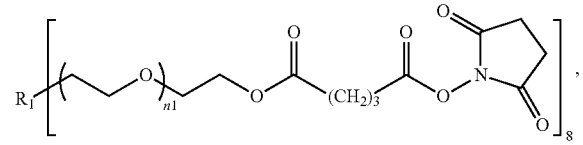

a second hydrogel precursor component comprising an aqueous medium comprising

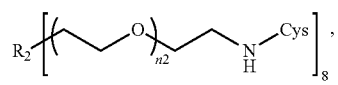

wherein $R_1$, $R_2$, n1 and n2 can be as described above, and a proline hydroxylase inhibitor precursor component comprising 1,4-DPCA coupled to a poly(alkylene oxide) block copolymer; mixing such precursor components to provide a hydrogel comprising such a coupled 1,4-DPCA component therein; and administrating such a hydrogel to a non-regenerative mammal presenting a tissue injury. Such administration can be distal to such an injury to provide 1,4-DPCA in an amount as can be sufficient to up-regulate HIF1a protein at the site of such an injury. Without limitation, in certain embodiments, administration can comprise subcutaneous, intraperitoneal and/or intramuscular injection. In certain such embodiments, administration can comprise multiple injections over time to stabilize a constitutive cellular level of HIF1a protein. Regardless, in certain embodiments of the sort described herein, a portion of such a proline hydroxylase inhibitor precursor component can be introduced to each of such first and second hydrogel precursor components prior to mixing.

In part, the present invention can also be directed to a therapeutic compound comprising, for instance, at least one 1,4-DPCA moiety coupled to via a cleavable (e.g., without limitation, hydrolyzable) moiety to a polymer component such as, for instance, a poly(alkylene oxide) component. Without limitation, in certain embodiments, such a polymeric component can comprise at least one ethylene oxide monomeric unit, at least one propylene oxide monomeric unit or a combination of such monomeric units. In certain such embodiments, such a component can comprise poly(ethylene oxide) or a copolymer of poly(ethylene oxide) and poly(propylene oxide). Without limitation, such a compound can comprise such a copolymer coupled at each terminus to a 1,4-DPCA moiety. In accordance with certain aspects of this invention, reference is made to the drug conjugate of Example 11, below. In certain other embodiments, such a compound can comprise a plurality of poly(ethylene oxide) and/or poly(propylene) oxide components coupled to a polyhydric core moiety. Without limitation, such a polyhydric core can be selected from hexaglycolic and tripentaerythritolic moieties. Regardless, one or more such poly(alkylene oxide) components can be further coupled to a 1,4-DPCA moiety. In accordance with certain aspects of this invention, reference is made to the drug conjugate of Example 18, below.

BRIEF DESCRIPTION OF THE DRAWINGS

The patent or application filed contains at least one drawing executed in color. Copies of this patent or patent application publication with color drawing(s) will be provided by the Office upon request and payment of the necessary fee.

FIGS. 1A, B, Ca-b, D, Ea-d, F, G and Ha-c. HIF1a levels are over-expressed and required in the MRL regenerative response. (A) Diagram of ear punch injury, derived histological sections and processed tissue samples is shown. (B-F) show HIF1a protein expression levels in MRL pre- and post-injury compared to B6 mice. (B) Pooled ear hole donuts (n=4) were processed for HIF1a western blot (WB) analysis using comassie blue (red on Odyssey) as loading control; N=2. (Ca-b) Ear tissue was used for HIF1a immunostaining and photomicrographs. Scale bar=0.1 mm. (D) Multiple samples for each timepoint (n=3-5; N=2) were quantitatively analyzed with highly significant differences p<0.01 (), at all timepoints between B6 and MRL responses peaking on da7. (Ea-d) Further confirmation of HIF1a levels was carried out using MRL and B6 mice backcrossed (BC4) to transgenic HIF1a-peptide-luciferase reporter mice. MRL.HIF-luc and B6.HIF-luc mice showed levels of luciferase activity with (F) IVIS-detected photon number on da7 in healing ear and whole mouse in MRL (red) compared to the B6 cross (blue), expressed as (p/sec/cm2/sr)=photons/sec/cm2/steradian. Both E and F are representative of experiments (N=3) of n=5 mice/group. (G-Ha-c) show requirement for HIF1a in MRL ear-hole closure regenerative responses with in-vivo RNAi against Hif1a (siHif1a) treatment. (G) SiHIF1a's (Qiagen) tested for blocking Hif1a mRNA in-vitro in MRL ear cells (n replicates=3); Gapdh is control (N=2) (H) SiHif1a_3 was used in-vivo in MRL.HIF-luc mice treated, ear-punched, and followed for 28 days. Mice were either injected subcutaneously with in-vivo-JETPEI-siHif1a_3 mixture da0-20 (15 ug/mouse; green) or PBS (red) with ear hole closure (Ha) highly significantly blocked, on da28 p=0.000016 (); (n=4 mice/group; N=2). (Hb) HIF1a levels determined by bioluminescence (dorsal and ventral) in reporter mice under treatment with siHif1a_3. (Hb,c) Number of photons detected on da14 in the injured ear (p=0.03) or whole mouse (p=0.04) with significant differences (*), by siHif1a_3 compared to control (n=4 samples/group; N=2).

DETAILED DESCRIPTION OF CERTAIN EMBODIMENTS

Figure 2A:
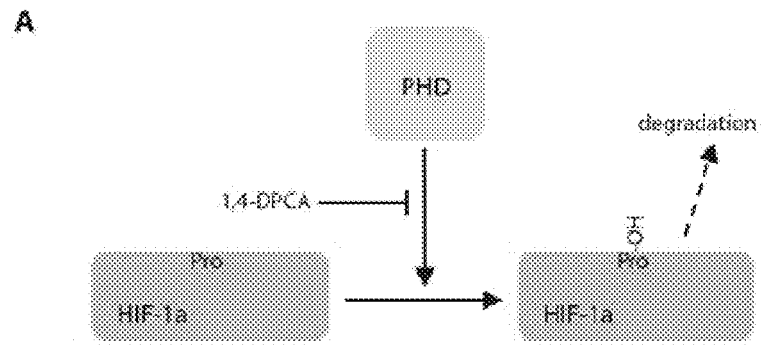
FIGS. 2A, B, C, Da-c and E. (A) Diagram showing that 1,4-DPCA acts as an inhibitor to PHDs and slows down degradation of HIF-1α. (B) Chemical structures of the drug delivery components including 1,4-DPCA, Pluronic F127, P8NHS, and P8Cys. (C) The presence of drug microcrystals does not interfere with the gelation kinetics of the hydrogel. (Da-c) The drug was encapsulated in the hydrogels to yield white and opaque cylindrical hydrogels (left) which when incubated in PBS released the drug leaving behind clear hydrogels (right). (E) In-vitro experiments showed that drug release occurred over several days for hydrogels containing 119-477 ug drug. Dashed lines represent total drug loading for each formulation. C and E show replicate samples (n=3).

Illustrating certain non-limiting embodiments of this invention, 1,4-DPCA (1,4-dihydrophenonthrolin-4-one-3-carboxylic acid), a well-defined PHD inhibitor, was used to stabilize the constitutive level of HIF1a protein. A locally-deliverable novel drug hydrogel construct was designed to slowly deliver 1,4-DPCA from the hydrogel over 4-10 days in-vitro. A functional measurement of in-vivo drug release, increase and stabilization of the constitutive level of HIF1a was observed over five days upon subcutaneous injection of 1,4-DPCA hydrogel. Multiple peripheral subcutaneous injections of 1,4-DPCA hydrogel over a 10-day period led to a regenerative response in non-regenerative Swiss Webster mice in a manner which fully emulates the MRL healing response (e.g., a pro-regenerative state with enhanced re-epitheliazation of the wound, induced progenitor cell phenotypes and enhanced tissue remodeling with increased MMP levels and a resultant basement membrane breakdown). (Both responses are inhibited by siHif.) The results demonstrate that controllable regeneration can be achieved by specifically manipulating the levels of HIF-1a protein using a peripherally deliverable drug/gel construct.

HIF1a Levels are Over-Expressed in the MRL Regenerative Response.

To determine HIF1a protein expression levels in MRL vs B6 mice, wounded ear pinnae (FIG. 1A) were examined by IHC and western analysis (FIG. 1B-D). Strikingly higher HIF1a levels were seen in MRL tissue post-injury with peak levels on day 7. For longitudinal studies, Hif1a reporter mice were created by backcrossing these two strains to the transgenic HIF1a-peptide-luciferase reporter mouse FVB.129S6-Gt(ROSA)26S, made by fusing luciferase to the domain of HIF1a that binds to pVHL in an oxygen-dependent way (ODD peptide). As seen in FIG. 1E-F, MRL.HIF-luc mice showed high levels of luciferase activity, a correlate of HIF1a protein levels, compared to the B6.HIF-luc mouse both pre-injury in the liver and post-injury throughout the body including the ear.

Inhibition of HIF1a Blocks MRL Ear Hole Closure.

To examine if HIF1a is necessary for ear hole closure, Hif1a siRNA was used. A panel of siHif1a's showed that 1 out of 4 tested siRNAs (siHif1a_3) could completely inhibit constitutive Hif1a mRNA levels in MRL fibroblasts, as well as fibroblasts from B6 and SW mice (FIG. 1G). SiHif1a_3 was then tested in-vivo in MRL.HIF-luc mice for its effect on ear hole closure and HIF1a levels. (Previous studies determined that a 30-day hole size of 0-0.4 mm diameter represented an MRL regenerative response, and 1.2-1.6 mm diameter hole represented a B6 wound repair and not a regenerative response.) As seen in FIG. 1H, ear hole closure was blocked by siHif1a_3 (FIG. 1Ha) and HIF1a levels as determined by bioluminescence were reduced in the reporter mouse whole body measurements as well as in the ear (FIG. 1Hb-c). From these results, the necessity of increased HIF1a levels for a regenerative response is clear and suggests the possibility that stabilization of HIF1a in non-regenerative mice may lead to a regenerative ear hole closure response.

Formulation of a Drug-Loaded Hydrogel Construct that Stabilizes HIF1a In-Vitro.

Figure 2B:
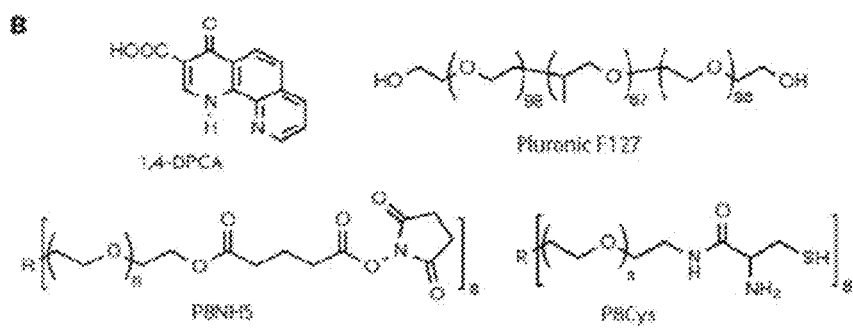
Figure 2C:
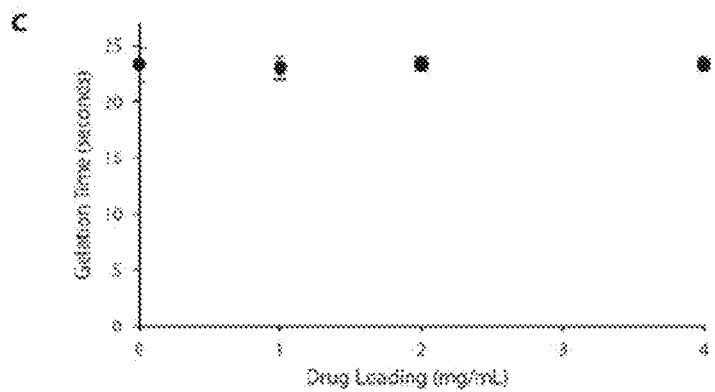

1,4-DPCA has been reported to be a potent inhibitor of the hydroxylases (PHDs and FIH) in-vitro and in-vivo at the protein level and rats given this compound showed inhibition of collagen hydroxylation and a reduction in collagen deposition. (See, Franklin et al, supra.) 1,4-DPCA can also stabilize HIF1a (FIG. 2A). As a delivery system for 1,4-DPCA, a polymer hydrogel system was devised. Composed of a crosslinked network of multi-armed polyethylene glycol, it is capable of rapid in-situ gel formation from a liquid precursor. This hydrogel system was chosen as the delivery vehicle due to its rapid gelation under physiological conditions, biocompatibility, and other favorable properties for in-vivo use. Drug-loaded hydrogels were formed by suspending polymer-stabilized 1,4-DPCA microcrystals in an aqueous mixture of hydrogel precursors P8Cys and P8NHS (FIG. 2B), which solidified rapidly upon mixing of both precursors to entrap the drug microcrystals within the hydrogel (FIG. 2C). In-vitro drug release studies demonstrated the slow and controlled delivery of 1,4-DPCA from the hydrogel over several days (FIG. 2D-E). Due to the poor solubility of 1,4-DPCA, crystals were surface-modified with F127 polymer to aid in homogeneous distribution throughout the hydrogel. Furthermore, entrapment of drug within the hydrogel helped to avoid cytotoxicity observed upon direct contact between cells and drug crystals. Due to the low solubility of 1,4-DPCA in water, drug release is likely by surface erosion from the crystals and diffusion through the hydrogel matrix.

Figure 3G:
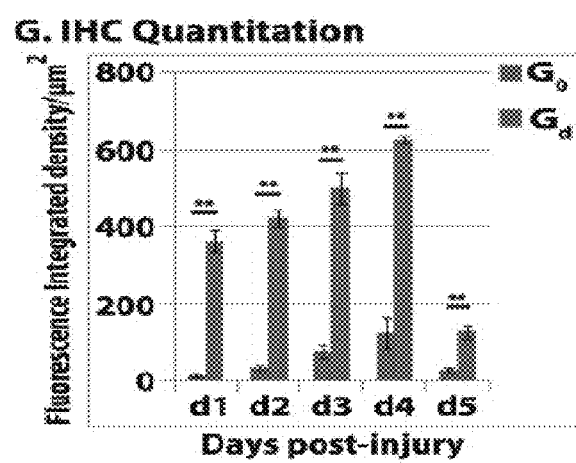
FIGS. 3Aa-c, B, C, D, E, Fa-f and G. 1,4-DPCA drug/gel stabilizes HIF1a, but not HIF2a, in-vitro and in-vivo. (Aa-c) B6 ear fibroblast-like cells were cultured with normal medium (Nor), gel alone ($G_0$) or 2 mg/ml drug/gel ($G_d$) using 100 ul total volume formed as a solid disc in 24 well plates. Addition of 1,4-DPCA drug/gel induced HIF1a protein, determined by immunostaining ($G_d$, green, Ac). Scale bar=50 um. (B) Cell lysates (n=3/lane) from (A) were used for western blot (WB) analysis for HIF1a (green) and HIF2a (red) levels compared to control protein a-tubulin (red) (N=4). (C) For activation of HIF1a target gene transcription, RT-PCR analysis of treated-B6 cell mRNA (n=3) from (A) examined multiple genes increased by 1,4 DPCA/gel including pro-angiogenic target genes Vegf and Hmox1, and pro-glycolytic targets Ldh-a, Pgk, Pdk1, and Glut1. Gapdh and 18S rRNA were used as internal controls for all RT-PCR reactions (N=4). (D-G) Mice treated with single injections of drug/gel and tested for HIF1a upregulation. (D) Schematic illustrates in-vivo treatment schedule. SW mice were ear-punched and injected several hours later in back of neck with either $G_0$ or $G_d$. Ear donut tissue for protein and IHC was collected on da1-5. In (E), hole donuts (n=6) were processed and western blot (WB) analysis was carried out with antibody to HIF1a (green) and analyzed (Odyssey) (N=3). The loading control is comassie-stained sample appearing red on the Odyssey. In (Fa-f), immunostaining of ear tissue with anti-HIF1a (green) and DAPI (blue) was carried out. (G) IHC quantitation for $G_0$ (blue) and $G_d$ (red) tissue show highly statistically significant differences, $p<0.01$ (**), at all timepoints (with mean+/−SE shown for all samples, n=5/treatment group, N=2).

B6 fibroblasts cultured with this drug/gel combination for 24 hrs. showed increased levels of HIF1a protein, but not HIF2a protein, both in the cytoplasm as well as in the nucleus as determined by IHC (FIG. 3A) and Western analysis (FIG. 3B) when compared to cells incubated with either gel alone or no drug/no gel. To determine the activation of HIF target gene transcription, RT-PCR analysis of mRNA from treated B6 cells revealed that multiple genes were specifically increased by 1,4-DPCA including the pro-angiogenic target genes Vegf and Hmox1 and the pro-glycolytic targets Ldh-a, Pgk, Pdk1, and Glut1 (FIG. 3C). Furthermore, all of these genes were blocked by siHif1a_3.

The Effect of the 1,4-DPCA Drug/Gel Construct In-Vivo.

To test the drug/gel construct for in-vivo function, non-regenerative SW mice were used. An initial attempt to directly apply the gel to the ear hole injury site failed as it could not be maintained on the wound. The drug/gel was injected subcutaneously at the base of the neck, distal from the wound, to achieve a pharmacological effect.

The kinetics of the effectiveness of the drug/gel construct in the injured ear was examined to determine how often re-injection would be necessary. After earpunching, a single injection (100 ul) of hydrogel containing either 2 mg/ml drug microcrystals ($G_d$) or 0 mg/ml drug microcrystals ($G_0$) was given plus an un-injected group. Ears were harvested daily for 5 days (FIG. 3D). The effect of 1,4-DPCA in-vivo on HIF1a expression levels in the ear, as determined by Western analysis (FIG. 3E) and by IHC (FIG. 3F,G), showed that HIF1a levels rose beginning on day 1, peaking on days 3-4 post-injection.

Multiple Injections of the Drug/Gel Construct Leads to a Regenerative Response.

Figure 4D:
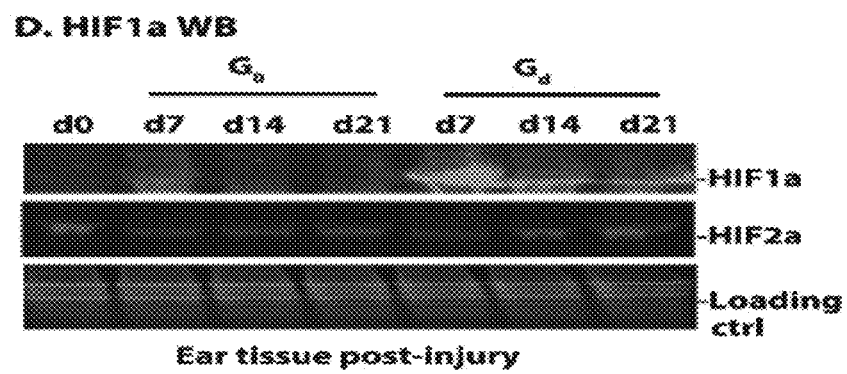
FIGS. 4A, Ba-d, Ca-d, D and E. Sequential injections of 1,4-DPCA drug/gel into mice at 5 day intervals shows a significant effect on healing. (A) Injection scheme diagram shows SW mice ear-punched and injected on da0, 5, and 10 into separate locations at base of neck, i.e. one site every five days (arrow). (Ba-d) Mice (n=16/group; N=4) were injected with either $G_0$ (0 mg/ml drug/gel, blue line) or $G_d$ (2 mg/ml drug/gel, red line) and followed for 35 days. Healing results with three injections of 2 mg/ml drug/gel are compared to $G_0$ on da35, p=1.93E-08 (). On the left are representative da35 ear pinnae (arrows point ear holes) (Ba, 0 mg drug/gel; Bb-c, 2 mg drug/gel). (Ca-d) Histological examples of Alcian blue-stained, da35 1,4-DPCA-treated closed ear holes (Ca,b) with the 2 mm area of original hole indicated and seen at higher magnification (Cc,d) (n=2). Areas of condensation are shown (black arrows); blue staining indicates presence of proteoglycans. (Cc) shows an earlier time-point after closure where epithelial cells (red arrow) persist in the new bridge region; in (Cd), the bridge is filled with mesenchymal cells. (D) Hole donuts (n=6) from punched ears treated with $G_0$ or $G_d$ were processed and western blot (WB) analysis (Odyssey) was carried out (N=3) with anti-HIF1a (green) or anti-HIF2a (red) antibodies; comassie protein staining is loading control (red). (E) On da20, in-vivo siHif1a treatment showed highly significant inhibition, p=7.79E-06 () comparing 1,4-DPCA-induced ($G_d$)/$G_0$ ear hole closure (red/green lines). siHif1a treatment compared to $G_0$-treated SW ears (green/blue) with significant, p=0.05 (*) inhibition. Highly significant p=0.01 (**) differences are seen comparing $G_0$ to $G_d$ (red/blue) (n=6-8; N=2).

Given data showing that day 7 post-injury is (approximately) the peak of HIF1a protein expression in MRL mice during healing and that HIF1a protein is still elevated in MRL on day 14 (FIG. 1D), multiple injections of drug/gel were given. Since a single injection of drug/gel had an effect on HIF1a levels through day 5, drug/gel and control gel were injected subcutaneously every 5 days (day 0, 5 and 10) into three adjacent sites in the back of the neck (FIG. 4A). In FIG. 4B, highly significant (on day 35 p=1.93E-08) as well as complete ear hole closure (FIG. 4C) was achieved via multiple injections of 2 mg/ml drug/gel ($G_d$) compared to 0 mg/ml drug/gel alone ($G_0$) with ongoing ear hole closure occurring up to day 35. Furthermore, western analysis (FIG. 4D) showed that although HIF1a is slightly up in $G_0$-treated SW mice on day 7 post-injury, it is dramatically up in $G_d$-treated SW on day 7, similar to MRL (FIG. 1B), and is still over-expressed up to day 21. On the contrary, HIF2a was barely affected by 1,4-DPCA in-vivo, consistent with in-vitro experiments using other cell types and showing no effect of 1,4-DPCA on HIF2a expression.

It should be noted that the injection of drug/gel at sites on the back of the neck to achieve ear hole regeneration suggests a systemic rather than a local/topical drug effect—a promising outcome since systemic activity may allow regeneration in less accessible anatomic sites and in a variety of tissues.

Distal Effects of the 1,4-DPCA Drug/Gel Construct.

Mice were injected subcutaneously (day 0, 5 and 10) into the left and right flank regions with drug/gel. Partial ear hole closure was achieved at 2 mg/ml but not 1 mg/ml. Though clearly effective, injection with 2 mg/ml drug/gel at the more distal flank sites led to lesser closure. We also examined long-term effects of gel with or without drug and no histo-pathological effects or weight changes were seen at 3 months.

SiHif Blocks the Regenerative Effect of 1,4-DPCA Drug/Gel In-Vivo.

Figure 4E:
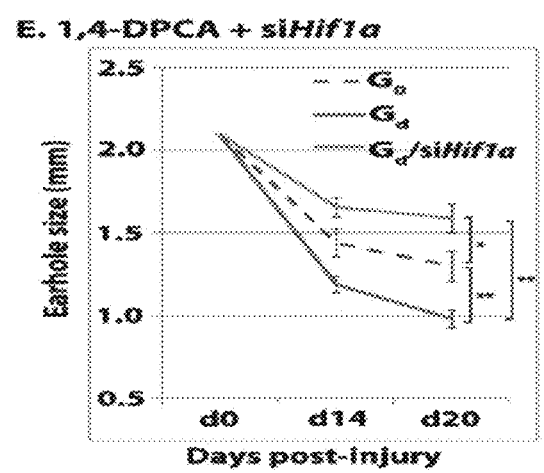

Finally, SW mice injected 3 times with 2 mg/ml of drug/gel at the back of the neck were at the same time injected with siHif1a_3 every other day for 20 days beginning on day 0. As seen in FIG. 4E, ear hole closure induced by 1,4-DPCA on day 14 and 20 was significantly inhibited by siHif1a to a greater extent than even $G_0$ by itself, indicating the HIF1a specificity of the regenerative effect on SW mice induced by 1,4-DPCA in-vivo, and a parallel to the HIF1a effect in spontaneously regenerating MRL mice.

Potential Mechanisms for HIF1a's Role in a Regenerative Response.

Figure 5A:
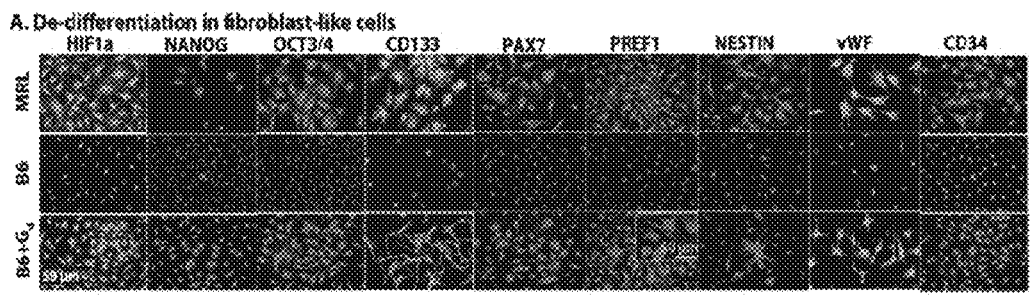
FIGS. 5A-C. HIF1a stabilization by 1,4-DPCA drug/gel induces stem cell markers in-vitro. (A) Cultured MRL (upper panels) and B6 (middle panels) cells grown on coverslips were immunostained with anti-HIF1, NANOG, OCT3/4, CD133, PAX7, PREF1 (DLK1), NESTIN, vWF and CD34. B6 cells were cultured with 2 mg/ml drug/gel (B6+$G_d$, lower panels) or 0 mg/ml drug/gel ($G_0$ not shown) for 24 hours (n=5-10 fields/coverslip; N=3). (B) QPCR results, consistent with IHC, show highly significant changes, $p<0.01$ (**) in mRNA levels for all molecules in drug-treated cell populations (n=3; N=3). (C) MRL cells (n=3 coverslips/grp) were treated with either siRNA control (left panel) or siHif1a (right panel) for 48 hours. The cells were immunostained with anti-NANOG antibody (N=2). All scale bars=50 um.
Figure 5B:
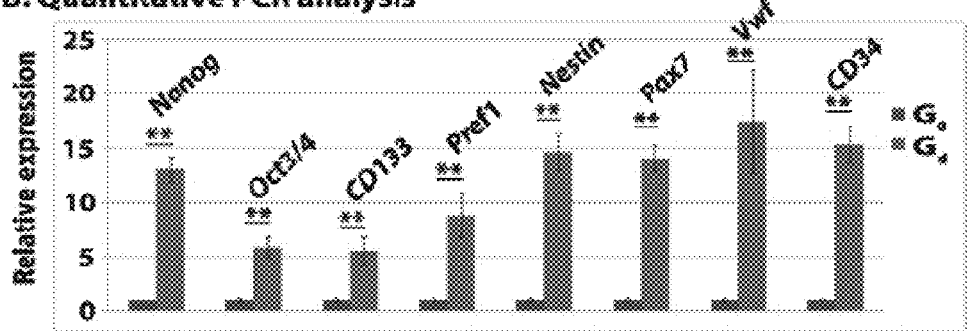
Figure 5C:
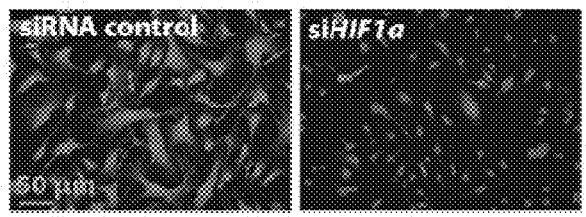

The striking ability of amphibians to achieve regeneration is often attributed to the ability of cells to de-differentiate and become more stem-like before blastema growth. The effect of HIF1a stabilization was examined for appearance of stem cell markers in-vitro, as it was previously found that NANOG and SOX2 up-regulated in regeneration-competent adult MRL mice and that MRL ear-derived fibroblasts in culture displayed multiple stem cell markers not expressed in B6 cells. In FIG. 5A, MRL fibroblasts (5A, first row) are positive for HIF1a and all immature markers tested; B6 fibroblasts (5A, second row) are negative, though rare positive staining was seen in dividing cells. However, B6 cells treated in-vitro with gel encapsulated 1,4-DPCA for 24 hours (5A, third row) become positive displaying both cytoplasmic and nuclear staining, indistinguishable from MRL cells with qPCR confirming these results. The B6 $G_0$ control was no different than the no-gel B6 cell control. QPCR results show highly significant differences between B6 fibroblasts treated with $G_0$ vs $G_d$ for all molecules tested (FIG. 5B). To address the specificity of HIF1a on these molecular markers in MRL, Hif1a siRNA-treatment (FIG. 5C) showed little NANOG staining compared to control-treated MRL cells, demonstrating a requirement for Hif1a, at least for NANOG. SiHif1a was tested in B6 cells after 1,4-DPCA treatment and also blocked multiple stem cell markers.

The role of HIF1a was explored in-vivo for multiple tissue phenotypes associated with regenerating amphibian as well as MRL tissue (FIG. 6). Without limitation to any one theory or mode of operation, re-epithelialization, de-differentiation, remodeling, lowered collagen crosslinking, blastema growth and re-differentiation were among the mechanisms for enhanced regeneration considered.

Very early and rapid re-epithelialization is a feature which distinguishes regeneration from wound repair. In the amphibian, re-epithelialization is complete within the first 12 hours and occurs between 1-2 days in the MRL, but not until 5-10 days in the B6 and other mouse strains. Here, SW mice treated with drug/gel showed re-epithelialization by day 2 not seen in $G_0$-treated mice (FIG. 6Aa-b). Epidermal HIF1a expression is seen on day 1 and followed by WNT5a expression on day 2 (FIG. 6. Ac-f), similar to drug-treated cells in-vitro (FIG. 6Ag-i). This may contribute to rapid cell migration and wound coverage.

Paralleling the response in-vitro (FIG. 5A), de-differentiation is also seen in-vivo after a single injection of 1,4-DPCA drug/gel construct, with the expression of stem cell markers in the injured dermis (FIG. 6Ba,b). NESTIN, OCT3/4, NF, and PAX7 expression by IHC (FIG. 6Bc-f) and qPCR (FIG. 6Bg) peaks at day 4-5 post-injury.

Tissue remodeling, including changes in extracellular matrix with breakdown of basement membrane is necessary for axolotl limb regeneration. Laminin, a major component of the basement membrane, is reduced in SW ear tissue after 1,4-DPCA treatment (FIG. 6Ca-b), and absent from the epithelial-mesenchymal border. MMP9, a major protease involved in laminin breakdown, increased after drug treatment (FIG. 6Cc) along with markers for inflammatory cells associated with tissue remodeling such as myeloperoxidase (MPO) and neutrophil-specific marker (Ly6G) (FIG. 6Cd-e) as well as mast cells.

Scarring, with increased collagen crosslinking, is associated with wound repair and is reduced during amphibian regenerative responses. After $G_d$ treatment, the picrosirius red (PSR) level, a marker of collagen cross-linking complexity, is reduced, but reversed by siHif1a treatment (FIG. 6Da-d). Besides the expected reduced level of PHD function by 1,4-DPCA, molecules such as loxl4 (lysyl oxidase-like 4) and Ctgf (connective tissue growth factor) are also reduced as shown by qPCR in SW ears after $G_d$ treatment (FIG. 6De) similar to MRL.

Figure 6E:
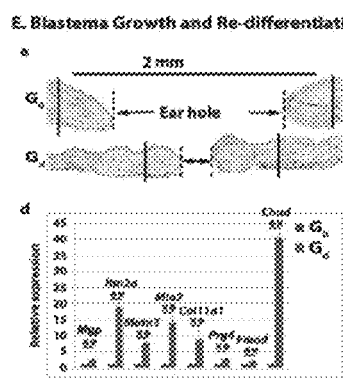
FIGS. 6Aa-i, Ba-g, Ca-e, Da-e and Ea-k. Key Elements of Regeneration. (Aa-i) Re-epithelialization of H&E-stained punched ear tissue (n=4/grp) is seen on da2 after injury from $G_0$ or $G_d$-treated SW mice (Aa,b) with black arrows showing incomplete (Aa) vs complete epidermis (Ab). Immunostaining is seen for HIF1a (Ac,d) and WNT5a (Ae,f) for $G_0$ (Ac,e) and $G_d$ (Ad,f) treated tissue; white arrows show epidermal staining. IHC of WNT5a protein expression induced in-vitro without (Ag) or with (Ah) 1,4-DPCA drug/gel; (Ai) shows western analysis of pooled tissue (n=3; N=2). (Ba-g) H&E sections (d4) illustrate the area of $G_d$-treated wound site de-differentiation (Ba,b, dashed lines). Immunostaining in $G_d$ and $G_0$ (insets) tissue include NESTIN, OCT3/4, NF, and PAX7 (Bc-f) (n=4), and qPCR results (Bg) show expression levels (n=3; N=3). (Ca,b) Tissue remodeling with laminin immunostaining to detect basement membrane (white arrow, inset) in $G_d$ vs $G_0$-treated tissue and (Cc-e) levels of MMP9, MPO, and Ly6G protein in $G_d$ vs $G_0$ (insets) are seen (n=4; N=3). In (A-C), blue is DAPI; red or green shows specific immunostaining. (Da-c) PSR staining shows da14 collagen cross-linking in (Da) $G_0$, (Db) $G_d$, (Dc) $G_d$+siHif1a-treated ear tissue with (Dd) quantitated polarized light results showing significant differences between $G_0$, $G_d$-treated and $G_d$ and $G_d$+siHIF1a-treated mice. (De) qPCR results show early (da2-3) Loxl4 and Ctgf expression in $G_d$ and $G_0$ samples (n=6/grp; N=2). (E) Blastema growth and re-differentiation into cartilage and hair follicles is seen after $G_d$ treatment. (Ea) Low magnification histological image of ear hole tissue stained with Alcian blue shows differences in chondrogenesis. Solid vertical lines indicate ends of cartilage, broken lines show soft tissue borders. (Eb) shows quantitation of soft tissue ear hole diameter, da35 with (Ec) a larger image of $G_d$-treated tissue showing two areas of new chondrogenesis (Eg,h) and new hair follicles (Ek). QPCR results show up-regulated chondrogenesis—(Ed) and hair follicle-associated (Ei) genes on da21 in $G_d$ vs $G_0$-treated tissue (n=3; N=3). Differences in (Ee) cartilage hole diameter and (Ef) cartilage area (a histomorphometric measurement of Alcian blue staining in new growth area) show highly significant differences. (Ej) The number of KRT14+ hair follicles in $G_d$-injected mice is compared to normal ear tissue or tissue from $G_o$-injected mice. All scale bars=0.1 mm except Ah=50 um. Statistical differences are indicated by (*) for significant with $p<0.05$ and (**) for highly significant with $p<0.01$.
Figure 6E:
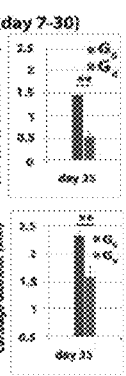
Figure 6E:
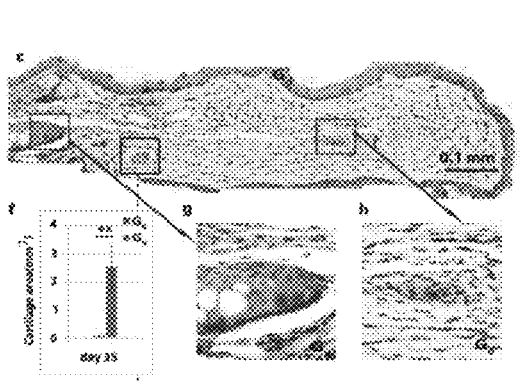
Figure 6E:
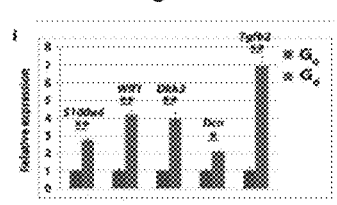
Figure 6E:
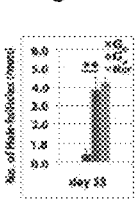
Figure 6E:
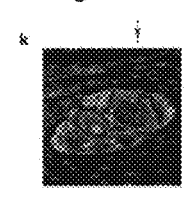
Figure 6E:
Figure 6E:
Figure 6E:
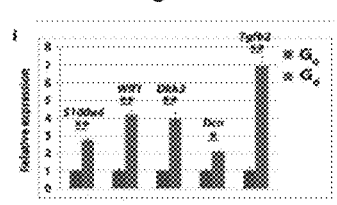
Figure 6E:
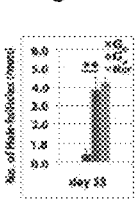
Figure 6E:
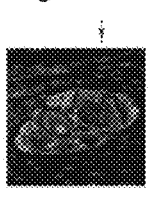

Blastema growth and re-differentiation with chondrogenesis and hair follicle growth, generally considered later events in the regenerative process, are also affected by 1,4-DPCA. As seen previously in FIG. 4B and now in FIG. 6Ea-c, a major difference in ear hole size with accompanying chondrogenesis and appearance of hair follicles (FIG. 6Ee-h) is apparent by day 35 after $G_d$ treatment of SW mice. Differences are seen histologically in tissue in the growth zone (FIG. 6Ec) as well as the end of the cartilage at the site of the original punch margin (FIG. 6Ee-h) which show areas of condensation, formation of a perichondrial region, and new chondrogenesis. Furthermore, chondrogenesis-associated molecules, Mgp, Itm2a, Matn3, Mia2, Col11, Prg4, Fmod, and Chad are upregulated on da21 in $G_d$-treated tissue (FIG. 6Ed). In addition, keratin (KRT)14-positive hair follicles are found in $G_d$ compared to $G_0$-induced tissue at a level seen in normal ear tissue (FIG. 6Ej-k) with up-regulation of specific molecular markers including S100a4, Wif1, Dkk3, Dcn, and Tgfb2 (FIG. 6Ei).

A major function of HIF1 is the activation of angiogenic target genes such as Vegf and an increase in angiogenesis. MRL cells and HIF1a-stabilized B6 cells, but not untreated B6 cells, were positive for vWF, an endothelial cell marker. It was also found that CD-31 positive cells and microvessels/capillaries were increased on day 7-post ear hole injury in MRL ears compared to B6. The same was seen in SW-injured ears after drug/gel treatment compared to control. RT-PCR demonstrates that Vegf and Hmox1 mRNA were up-regulated as well.

To test the requirement for angiogenesis in ear hole closure, endostatin was administered to 1,4DPCA drug/gel-treated SW mice. Endostatin, like siHif1a_3, showed almost complete blockage of ear hole closure in these mice. However, siHif1a_3 and endostatin had differing effects on the expression of molecular markers of stem cell state, angiogenic markers, tissue remodeling and inflammation, allowing a hierarchal ordering of some processes central to regeneration. On day 7 post-injury and treatment, a near complete absence of HIF1a, CD31, and OCT ¾ staining was observed for both endostatin and siHif1a_3. A decrease in MMP-9, MPO, and a neutrophil specific-marker was found with siHif1a_3 but to a lesser degree with endostatin. On the other hand, a greater degree of inhibition of laminin staining was found with endostatin than with siHif1a_3.

Following its discovery by Semenza, there has been a growing recognition that HIF1a is a master regulator of cell functions from regulating $O_2$ levels to aerobic glycolysis, cell migration and inflammation. In this report, we propose another role for HIF1a, i.e. as a central actor in mammalian regeneration. Given HIF1a's many known functions in cellular processes that distinguish tissue regeneration from a scarring (tissue repair) response, it was natural to explore HIF1a's role in regenerative wound healing in the MRL mouse, a strain which uses aerobic glycolysis as its basal metabolic state and is a spontaneous regenerator of multiple tissue types. Furthermore, a recent genetic fine mapping study showed that RNF7, an E3 ligase necessary for HIF1a ubiquination, is a strong candidate gene for LG/J ear hole regeneration, is down-regulated in both LG/J and MRL mice, and should predictably lead to high HIF1a levels. As shown in the results, HIF1a is upregulated in unwounded MRL versus B6 and SW mice, is further increased post-wounding, and siHif1a blocks MRL ear hole closure. To determine the effect of high levels of HIF1a in non-regenerative Swiss Webster mice, the HIF1a-stabilizing drug 1,4-DPCA was delivered subcutaneously via a hydrogel construct, inducing ear hole closure when given both proximally and distally. As in MRL, in-vivo siRNA against Hif1a blocks this drug-induced regenerative response supporting the conclusion that, at least in mice, up-regulation of HIF1a levels is sufficient to achieve appendage regeneration.

Creating an effective delivery system for 1,4-DPCA presented a major chemical challenge. A problem is the low solubility of this molecule and, hence, the inability to deliver a biologically effective dosing. This was overcome by the use of block copolymer-stabilized 1,4-DPCA microcrystals embedded in a hydrogel. In-vitro results using differentiation and other markers led to the belief that this was a promising in-vivo approach. A regenerative response identical to that observed in MRL mice was achieved using this construct.

Recent data has shown that two inhibitors of PHDs which block HIF degradation, DMOG and DFX, enhance diabetic wound healing when applied directly to the wound site. However, the induction of a regenerative response requires far higher levels of HIF1a and has not been reported. Results reported herein describe a novel structure and method of drug delivery using a drug crystal and hydrogel that may be effective to treat injury through a systemic route. The idea of inducing tissue regeneration via a simple, minimally invasive subcutaneous administration of drug carrier at a peripheral site is both attractive and a significant departure from previous tissue regeneration paradigms.

The use of 1,4-DPCA-hydrogels has several advantages. They slowly deliver large amounts of 1,4-DPCA from the hydrogel over 4-10 days depending on the gel formulation and drug dose when tested in-vitro, and cause increased HIF1a protein levels in-vivo for up to 5 days. Also, entrapping the drug microcrystals within the hydrogels avoids potential cytotoxicity associated with direct uptake of drug crystals by cells. In terms of specificity, 1,4-DPCA interacts with and blocks PHD function and could affect not only HIF1a, but HIF2a as well as other target molecules. However, HIF2a is not affected by the drug gel construct in-vitro, in either fibroblasts or endothelial cells, nor is it increased in ear tissue after $G_d$ treatment. Furthermore, siHif1a blocked all regenerative phenotypes examined.

Limb regeneration in amphibians generally centers on the formation and growth of the blastema, a tissue structure seen in the embryo and regenerating tissue and made up of a mass of undifferentiated pluripotent cells which can proliferate and then produce a copy of the lost structure. This begins with rapid coverage of the wound by epithelial cells, reforming in the absence of a basement membrane. Undividing mesenchymal cells form under the new epidermis as the accumulation blastema and then divide, produce tissue elongation, and finally re-differentiate into lost parts.

HIF1a-regulated gross regenerative effects in MRL and drug-treated SW mice emulates molecular and cellular correlates of the amphibian blastema and de-differentiation followed by tissue remodeling and proliferation and later followed by re-differentiation components of the classical regeneration process. HIF1a is expressed at its highest levels in the early phase of the regenerative response. This is associated with the accumulation blastema period forming through cell migration and de-differentiation in regenerating tissue and is consistent with up-regulation of molecules such as WNT5a involved in cell migration, and NANOG and OCT3/4 as de-differentiation markers peaking at approximately day 7 post-injury, after which the levels of these molecules fall and proliferation proceeds. The developmental state occurs in low levels of oxygen. This hypoxic state results in increased HIF1a, increased morphogenesis, and increased presence of stem cells with the induction of multiple ESC-associated genes and differentiation markers. MRL ear tissue showed unusual expression of a range of diverse stem cell markers both in-vitro and in-vivo including NANOG, SOX2, OCT3/4, CD34, and CD133, all pluripotency markers; NESTIN, a neuronal stem and progenitor cell marker; PAX7, a satellite muscle-associated stem cell marker; WNT5a, an early marker involved with migration, and PREF1 or DLK1, a pre-adipocyte and hepatocyte stem cell marker. This was not found in non-regenerator B6 or SW tissue. HIF1a stabilization by 1,4-DPCA led to increased levels of all of these differentiation markers, though only transiently, reducing long-term concerns associated with potential treatment. SiHif1a blocked NANOG expression in MRL cells suggesting that all of these markers are due to increased HIF1a levels in this mouse; siHif1a blocked many of these markers in 1,4-DPCA+siHif1a-treated non-regenerative cells and tissues. Besides a hypoxic environment and elevated HIF1a, stem cells require a glycolytic metabolism seen in MRL mice and other regenerating models. Surprisingly, HIF2a, reported to control expression of Nanog and Oct3/4, is not elevated, though a recent study shows other controlling factors such as miR-302.

To further confirm that this drug-induced regenerative response faithfully emulates the phenomena observed in the MRL mouse, and key processes observed for many years in classical regenerators such as newts and axolotls, other known HIF1a functions were examined. These include an enhanced tissue remodeling response, increased MMP levels, a de-differentiated cellular signature, increased glycolytic enzymes, increased components of the inflammatory response and increased angiogenesis leading to ear hole closure.

Next, tissue remodeling necessary for ECM changes in regenerating amphibian limb blastemas shows increased MMP levels and no basement membrane which if restored using retinoic acid treatment produces scar with no regeneration. HIF1a regulates MMPs which regulate extracellular matrix levels including laminin and basement membrane-remodeling proteins. Like MRL, 1,4-DPCA-treated SW mice show increased MMP9 levels and a vanishing basement membrane (FIG. 6Ca,b). A second regeneration-promoting effect of 1,4-DPCA on PHDs is inhibition of collagen hydroxylation leading to reduced scarring and increased degradation. Other HIF1a-regulated remodeling molecules include lysyl oxidase and collagen prolyl (P4HA1,2) and lysyl (PLOD2) hydroxylases which increase ECM stiffness and alignment. MRL and 1,4-DPCA-treated SW mice express reduced levels of lox14 and ctgf.

The developmental state occurs in low levels of oxygen and this hypoxic state results in increased HIF1a, increased morphogenesis, and increased stem cells with the induction of multiple ESC-associated genes and differentiation markers. MRL ear tissue showed unusual expression of a range of diverse stem cell markers both in-vitro and in-vivo including NANOG, SOX2, OCT3/4, CD34, and CD133, all pluripotency markers; NESTIN, a neuronal stem and progenitor cell marker; PAX7, a satellite muscle associated stem cell marker; WNT5a, an early cell marker; and PREF1 or DLK1, a pre-adipocyte and hepatocyte stem cell marker. This was not found in non-regenerator mouse tissue from either B6 or SW.

However, HIF stabilization by 1,4-DPCA led to increased levels of all of these differentiation markers, though only transiently, making this less of a concern with treatment. SiHif blocked NANOG expression in MRL cells suggesting that perhaps all of these markers are due to increased HIF1a levels in this mouse and siHif blocked OCT3/4 post 1,4-DPCA treatment. Besides an hypoxic environment and elevated HIF1a, stem cells require a glycolytic metabolism, seen in the MRL mouse and other regenerating models. Though it is not clear why this metabolic state is necessary, Cripto/GRP78 may play a role. The virtual identity of all of the above markers in MRL ear cells and the 1,4-DPCA-treated SW cells dramatically confirms the unity of a regeneration-type response in these models.

Re-differentiation of mesenchymal tissue with formation of new cartilage and hair follicles is seen in regenerating tissue. In MRL, elastic and articular cartilage begins at about 1 month and can fully regenerate within 3-4 months. With 1,4-DPCA treatment, the new growth area shows chondrogenesis by day 35, with upregulation of multiple chondrogenesis markers including those in chondrogenic precursor cells and molecules found in cartilage extracellular matrix. Hair follicles are also found in the new growth area at a level seen in normal tissue and multiple markers of bulge-derived keratinocyte stem cells and cells in the epithelial sac involved in regeneration are expressed.

Down-regulation of HIF1a inhibits inflammation. It has been shown using a Hif1a conditional knockout mouse that HIF1a is required and controls the inflammatory response through regulation of glycolysis, a state necessary for myeloid (including neutrophils and macrophages) survival and function with effects specifically on aggregation, invasion, motility, and cutaneous inflammation. NSAIDs such as the COX2 inhibitors indomethacin, meloxicam and ibuprofen, which negatively regulate inflammation, also inhibit HIF1a through the up-regulation of pVHL expression. Down-regulation of HIF1a in a HifKO mouse has been shown to heal burn wounds poorly with a concomitant reduction in angiogenesis and SDF1. As shown here, MPO, a marker of inflammation, and a neutrophil specific marker are up-regulated in the non-regenerative SW given 1,4-DPCA similar to the MRL mouse.

Previous studies showed the role of angiogenesis in the regenerative response such as an AGF (angiopoietin-related growth factor) tg mouse with increased vascular and epithelial proliferation and positive ear hole closure and an angpt1 (angiopoetin1) ko mouse (angpt1 negatively regulates angiogenesis) with positive ear hole closure, and the known effects of HIF1a on angiogenesis. Comparing endostatin, a broad spectrum angiogenesis inhibitor, to siHif for their ability to block 1,4 DPCA-induced hole closure, it was found that all of the phenotypes described above were affected by siHIF and endostatin, some similarly and some oppositely allowing us to generate a preliminary map of effector function.

Three molecules, HIF1a, CD31, and OCT3/4, were inhibited equally by siHif and endostatin. This is to be expected for CD31 which reacts with endothelial cells and vessels as well as for HIF1a which has been previously shown to be down-regulated by endostatin. However, the equal blocking of OCT3/4 expression with endostatin treatment suggests that OCT3/4 is downstream of endostatin and angiogenesis. In contrast, unlike siHIF, endostatin did not inhibit MPO and anti-neutrophil marker (markers of inflammation) or MMP9 (remodeling) suggesting that these effector functions are upstream of angiogenesis and stem cells/de-differentiation.

Finally, laminin expression was most affected by endostatin which was surprising as it is considered to be involved with remodeling. However, it is consistent with laminin expression in blood vessels which when vessel formation is blocked should reduce laminin levels.

These data, taken together, as highlighted by the virtual identity of all of the differentiation markers in both MRL ears and 1,4-DPCA-treated B6 cells as well as drug-treated SW ears strongly supports the unity of the spontaneously regenerating MRL mouse model, the 1,4-DPCA-induced regeneration in SW mice and classical amphibian regenerators observed in nature.

EXAMPLES OF THE INVENTION

The following non-limiting examples and data illustrate various aspects and features relating to the methods and/or systems of the present invention, including the preparation of various hydrogels as are available through the synthetic methodologies described or referenced herein. In comparison with the prior art, the present methods and systems provide results and data which are surprising, unexpected and contrary thereto. While the utility of this invention is illustrated through the use of several hydrogel systems and precursor components, and PHDs which can be used therewith, it will be understood by those skilled in the art that comparable results are obtainable with various other hydrogel systems, precursor components and therapeutic agents, as are commensurate with the scope of this invention.

Inbred mouse strains were used to study the effect of a small molecule inhibitor of PHD on in-vitro and in-vivo levels of HIF1a, and the impact of this on quantitative regenerative ear hole closure phenotypes. In animal studies, 2.1 mm ear hole punch wounds were created and a 1,4-DPCA-containing hydrogel was subcutaneously implanted in the back of the neck of mice at multiple time-points. Healing was monitored by measuring hole diameters. Endpoints of the study were previously determined to be 30+ days post-injury and included key indices of tissue regeneration such as blastema formation, epithelial, dermal, and cartilaginous wound closure with hair follicle replacement plus multiple molecular markers of cellular de-differentiation, re-differentiation, and stem cell state. These parameters were determined by physical measurements of wound closure, standard tissue histology and histomorphometry, and gene expression using quantitative immunohistochemistry, western analysis, and qPCR. The experimental groups were coded and different laboratory personnel were involved in injuries, injections, phenotyping and data analysis.

Example 1

Animals and In-Vivo Procedures.
MRL/MpJ and Hif1a ODD-luciferase reporter (FVB.129S6-Gt(ROSA)26Sortm2(HIF1A/luc)Kael/J) mice were obtained from Jackson Laboratories (Bar Harbor, Me.); C57BL/6 (B6) mice were from Taconic Laboratories (Germantown, N.Y.); Swiss Webster (SW) mice were from Charles River (New York, N.Y.). Mice were used at approximately 8-10 weeks in all experiments under standard conditions at the Wistar Institute Animal Facility (Philadelphia, Pa.) and the protocols were in accordance with NIH Guide for the Care and Use of Laboratory Animals. Through-and-through ear hole punches were carried out as previously described.

Example 2

IVIS Luciferase Scanning.
To detect luciferase expression in-vivo, mice were given a single i.p. injection of D-luciferin (37.5 mg/kg, Gold Biotechnology Inc) in sterile water. Fifteen minutes later, mice were anesthetized using isoflurane and placed in a light-tight chamber equipped with a charge-coupled device IVIS imaging camera (Xenogen, Alameda, Calif.). Photons were collected for a period of 1-5 min, and images were obtained by using LIVING IMAGE software (Xenogen) and IGOR image analysis software (WaveMatrics, Lake Oswego, Oreg.). HIF1a ODD luc expression after ear punching was determined in MRL and B6 mice backcrossed to the transgenic HIF1a-peptide-luciferase reporter mouse FVB.129S6-Gt(ROSA)26S, made by fusing luciferase to the domain of HIF1a that binds to pVHL in a oxygen-dependent way (ODD peptide) mice and selected for luciferase positivity.

Example 3

Tissue Culture.
Primary ear dermal fibroblast-like cells were established from MRL and B6 mice and grown in DMEM-10% FBS supplemented with 2 mM L-glutamine, 100 IU/mL penicillin streptomycin and maintained at 37° C., 5% $CO_2$, and 21% $O_2$. Cells were split 1:5 as needed to maintain exponential growth and avoid contact inhibition. Passage numbers were documented and cells from early passages (<P20) frozen in liquid nitrogen and used in the described experiments.

Example 4

Western Analysis.
Ear tissue samples (3 ear hole donuts/ear from 3 separate mice) were homogenized in radio-immunoprecipitation assay buffer (50 mM Tris-HCl pH 7.6, containing 150 mM NaCl, 1% Triton X-100, 1% sodium deoxycholate, 1 mM EDTA and 0.1% SDS) with 1 mM PMSF and a protease inhibitor cocktail (Sigma). Samples with equal amounts of protein (about 40 μg) were loaded into a NuPAGE 4-12% Bis-Tris gradient gel or 8% Bis-Tris gel (Life Technologies, Grand Island, N.Y.), electrophoresed and then electro-transferred onto a PVDF-FL membrane (Immobilon, Billerica, Mass.). The membrane was subsequently blocked with Odyssey blocking buffer (LI-COR, Lincoln, Nebr.), probed with primary antibodies (HIF1a (10006421, Cayman Chemical, Ann Arbor, Mich.), HIF2a (NB100-132B, Novus, Littleton, Colo.), Wnt5a (BAF645, R&D System) or a-Tubulin (Sigma) overnight at 4° C., then further incubated with Alexa Fluor-labeled secondary antibodies (IRDye 800CW goat-anti rat or IRDye 800CW goat-anti rabbit (LI-COR, Lincoln, Nebr.) for 1 hr and scanned using the Odyssey system (LI-COR, Lincoln, Nebr.).

Example 5

Hif-1a siRNA Transfection In Vitro and In Vivo.
B6, SW, and MRL ear fibroblast-like cells at 70% of confluence were transfected with 100 nM of 4 different HIF-1a siRNAs (SI00193025, SI00193032, SI00193011, SI00193018) purchased from Qiagen and scramble siRNA (sc-37007, Santa Cruz Biotechnologies), using Lipofectamine 2000 according to the manufacturer's protocol. Transfected cells were examined for the knockdown efficiency after 48 h of transfection. siRNA Mm_Hif1a_3 (SI00193025) was selected for the in vitro experiments due to its high efficiency. In vivo, siRNA Mm_Hif1a_3 was used for HIF-1a inhibition. SiHif at 75 mg/kg body weight was mixed with Jetpei (Polyplus, Genycell) following manufacturer's instructions and was then injected into animals subcutaneously every 48 h.

Example 6

RNA Isolation and RT-PCR.

Total RNA from ear fibroblast-like cells or ear hole donuts was prepared with Qiagen RNeasy kit (Qiagen) according to the manufacturer's guidelines. First strand cDNA was synthesized from 1 μg of RNA using the Superscript First-Strand Synthesis System (Invitrogen, Carlsbad, Calif.) according to the manufacturer's instructions. qPCR was performed with SYBR green PCR Master Mix (Applied Biosystems, Life Technologies). In brief, a 20 μl mixture was used containing 10 μl SYBR Green PCR master mix, 1 μl forward and reverse primer, 6 μl sterile water, and 2 μl of complementary DNA template. A negative control (non-template control) was performed in each run. The real-time PCR was performed using a Quant Studio 6 Flex (Applied Biosystems) according to the manufacturer's instructions. All data were normalized to 18S rRNA and quantitative measurements were obtained using the $\Delta\Delta C_T$ method. (The primers used are listed with the kit, but not shown, here.

Example 7

Immunohistochemistry.

The methods used were performed as previously described. Tissue from normal ears were fixed with Prefer fixative (the active ingredient is glyoxal) (Anatech) overnight and then washed in $H_2O$. Tissue was embedded in paraffin and 5-μm thick sections cut. Before staining, slides were dewaxed in xylene and rehydrated. Antigen retrieval was performed by autoclaving for 20 min in 10 mM Sodium Citrate, pH 6.0. Tissue sections were then treated with 3% $H_2O_2$ and nonspecific binding was blocked with 4% BSA (A7906; Sigma) for 1 h. The primary antibodies and matched secondary antibodies used for IHC were shown in Table 2. For immunocytochemistry staining, primary ear skin fibroblasts were grown on coverslips in DMEM with 10% FBS at 37° C. in a humidified 5% $CO_2$ incubator. The coverslips were rinsed with 1×PBS, the cells were fixed in cold methanol (−20° C.) for 10 min, rinsed with 1×PBS, treated with 0.1% Triton-X100, and then incubated with the appropriate primary and secondary antibodies (Table 1). Photomicrographs were produced using the fluorescent microscope (Olympus AX70) and a Spot camera with bundled software.

For histological stains, tissue sections were treated the same as above and then stained with Hematoxylin (Leica Microsystems, #3801562) and Eosin (Leica Microsystems, #3801602), Picro-Sirius Red (Poly Scientific, cat. #s2365), Alcian blue (1% in 3% acetic acid (Polyscience, Bay Shore, N.Y., cat #S111A), or toluidine blue O (Allied Chemical, Morristown, N.J., cat. #NA0652), counterstained with Kernechtrot (Polyscience, Bay Shore, N.Y., cat #S248). The slides were washed, rehydrated, cleared with Xylene and coverslipped with Permount mounting media (Fisher, SP15-500). Staining was visualized using an Olympus (AX70) microscope in bright field for H&E and under polarized light for Picro-Sirius Red.

For quantitation of IHC signal, the method used was previously described. Briefly, we used ImagePro v4.0 for image analysis by selecting positive staining from multiple areas in the sections. The number of "positive staining" pixels was determined. The area was expressed in square microns and the final data were expressed as IHC staining signal per square micron. The mean of 2-6 samples were plotted and standard errors calculated.

TABLE 1

Antibodies used for Immunostaining

| | 1st antibody | | | 2nd antibody All From Molecular | | | |
|---|---|---|---|---|---|---|---|
| | Company | Cat. no. | Dilution | Probe | Company | Cat. no. | Dilution |
| HIF1a | Abcam | ab2185 | 1:1000 | Alexa Fluor 488 goat anti-rabbit IgG | Molecular Probe | A11008 | 1:200 |
| Nanog | Calbiochem | SC1000 | 1:150 | Alexa Fluor 568 goat anti-rabbit IgG | Molecular Probe | A11036 | 1:400 |
| Oct-3/4 | Santa Cruz | sc-5279 | 1:150 | Alexa Fluor 568 rabbit anti-mouse IgG | Molecular Probe | A11061 | 1:400 |
| CD133 | Chemicon | MAB4310 | 1:100 | Alexa Fluor 594 goat anti-rat IgG | Molecular Probe | A11007 | 1:200 |
| CD34 | Bioss | bs-0646R | 1:200 | Alexa Fluor 568 goat anti-rabbit IgG | Molecular Probe | A11036 | 1:300 |
| Wnt5a | R&D Systems | BAF645 | 1:150 | Alexa Fluor 568 donkey anti-goat IgG | Molecular Probe | A11057 | 1:200 |
| PAX7 | R&D Systems | MAB1675 | 1:50 | Alexa Fluor 568 rabbit anti-mouse IgG | Molecular Probe | A11061 | 1:400 |
| Pref-1 | MBL International | D187-3 | 1:10 | Alexa Fluor 594 goat anti-rat IgG | Molecular Probe | A11007 | 1:200 |
| Nestin | DHSB | | 1:50 | Alexa Fluor 594 goat anti-mouse IgG | Molecular Probe | A11005 | 1:200 |
| vWF | Dako | A0082 | 1:100 | Alexa Fluor 488 goat anti-rabbit IgG | Molecular Probe | A11008 | 1:200 |

TABLE 1-continued

Antibodies used for Immunostaining

| | 1st antibody | | | 2nd antibody All From Molecular Probe | | | |
|---|---|---|---|---|---|---|---|
| | Company | Cat. no. | Dilution | Probe | Company | Cat. no. | Dilution |
| Nefh | Sigma | N0142 | 1:200 | Alexa Fluor 568 rabbit anti-mouse IgG | Molecular Probe | A11061 | 1:400 |
| Lamc2 | Sigma | L-9393 | 1:50 | Alexa Fluor 568 goat anti-rabbit IgG | Molecular Probe | A11036 | 1:1000 |
| MPO | NeoMarkers | RB-373A1 | 1:70 | Alexa Fluor 488 goat anti-rabbit IgG | Molecular Probe | A11008 | 1:200 |
| Anti-Neutrophil mAb | Cedarlane | CL8993F | 1:40 | FITC mouse anti-rat IgG | Jackson ImmunoResearch lab | 212096082 | 1:100 |
| MMP9 | Sigma | M9555 | 1:200 | Alexa Fluor 568 goat anti-rabbit IgG | Molecular Probe | A11036 | 1:200 |

Example 8

Data Analysis.

All experiments were repeated multiple times (N) and the data represent pooled samples for western analysis and qPCR, and individual samples in healing studies and tissue analysis (n) as indicated in figure legends. All experiments employed inbred mouse strains reducing individual-to-individual variation. Student's t-test was carried out to compare differences of means from independent samples between two groups. The ANOVA test was performed to determine if there were significant differences among the means of more than two groups. If the p-value from ANOVA analysis was significant, then the post-hoc Tukey test was applied to compare the mean between each group. P-values less than or equal to 0.05 were considered as significant and equal or less than 0.01 considered highly significant. All error bars shown on graphs represent standard errors (SE) except in FIG. 2 where the standard deviation (SD) is used. The software used for ANOVA analysis and the post-hoc Tukey test is R, version 2.14.1. All other statistical analyses were done using Microsoft Excel 2010.

Example 9

Figure 7:
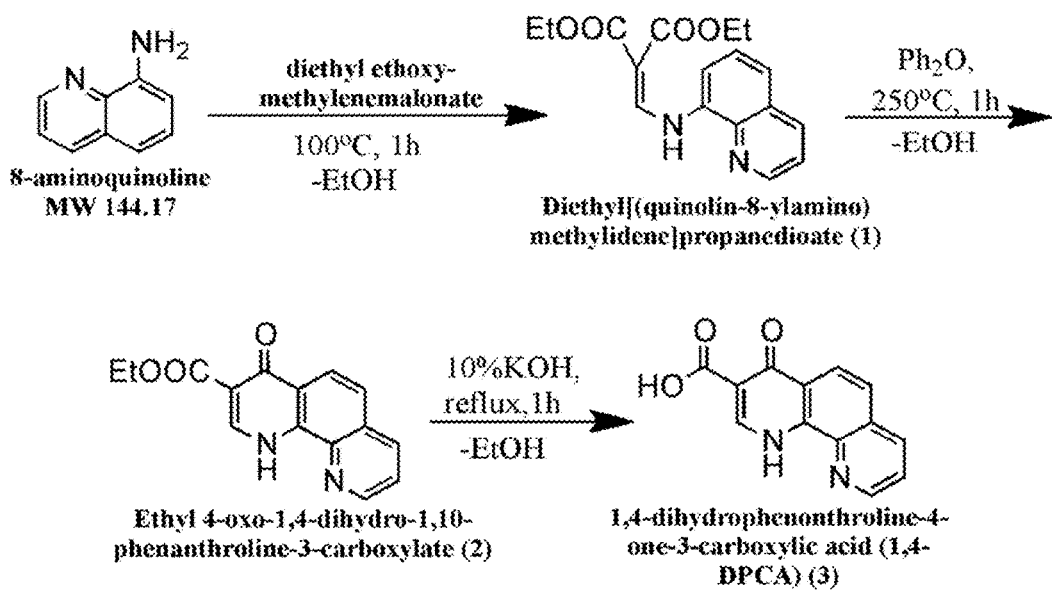
FIG. 7. Synthesis of 1,4-DPCA was accomplished in three steps. The synthetic scheme and the chemical structures of the three main products (1-3) are shown here.

With reference to FIG. 7, the compound 1,4-DPCA was prepared as follows:

Example 9a

Synthesis of Diethyl[(quinolin-8-ylamino)methylidene]propanedioate (1).

1 was prepared using a modified protocol described previously in the literature. 8-aminoquinoline (3.31 g, 22.9 mmol) and diethyl ethoxymethylenemalonate (4.63 mL, 22.9 mmol) were heated to 100° C. for 1 hour and then cooled to 80° C. and 20 mL methanol was added. The crystallized product was washed twice with 20 mL MeOH and dried on high vacuum to afford 1 (5.68 g, 18.1 mmol, 79%) as green-brown needles. $^1$H NMR (500 MHz, Chloroform-d), δ, ppm (J, Hz): 12.37 (1H, d, $^3J_{NH,=CH}$=14.3, NH); 8.97 (1H, dd, $^3J_{2,3}$=4.3, $^4J_{2,4}$=1.7, H-2); 8.80 (1H, d, $^3J_{=CH,NH}$=14.3, =CH); 8.18 (1H, dd, $^3J_{4,3}$=8.3, $^4J_{4,2}$=1.7, H-4); 7.55 (3H, m, H-5,6,7); 7.49 (1H, dd, $^3J_{3,4}$=8.3, $^3J_{3,2}$=4.2, H-3); 4.42 (2H, q, $^3J_{OCH2,CH3}$=7.1, (Z)-ester OCH$_2$); 4.30 (2H, q, $^3J_{OCH2,CH3}$=7.1, (E)-ester OCH$_2$); 1.44 (3H, t, $^3J_{CH3,OCH2}$=7.1, (Z)-ester CH$_3$); 1.37 (3H, t, $^3J_{CH3,OCH2}$=7.1, (E)-ester CH$_3$).

Example 9b

Synthesis of Ethyl 4-oxo-1,4-dihydro-1,10-phenanthroline-3-carboxylate (2)

2 was prepared using a modified protocol described previously. 1 (5.50 g, 17.5 mmol) was added to diphenylether (55 mL) and refluxed (250° C.) for 1 hour, then cooled to room temperature and collected through filtration. The precipitate was triturated twice with 25 mL petroleum ether (b.p. 80-110° C.) followed by washing with 10 mL of cold Et$_2$O. The precipitate was dried on high vacuum overnight to afford 2 (2.05 g, 7.65 mmol, 44%) as a beige powder. $^1$H NMR spectrum (500 MHz, DMSO-d$_6$), δ, ppm (J, Hz): 12.88 (1H, s, NH); 9.10 (1H, dd, $^3J_{2,3}$=4.3, $^4J_{2,4}$=1.6, H-2); 8.57 (1H, dd, $^3J_{4,3}$=8.3, $^4J_{4,2}$=1.6, H-4); 8.54 (1H, s, H-8); 8.22 (1H, d, $^3J_{6,5}$=8.8, H-6); 7.90 (1H, d, $^3J_{5,6}$=8.8, CH, i); 7.84 (1H, dd, $^3J_{3,4}$=8.3, $^3J_{3,2}$=4.3, H-3); 4.25 (2H, q, $^3J_{OCH2,CH3}$=7.1, OCH$_2$); 1.30 (3H, t, $^3J_{CH3,OCH2}$=7.1, CH$_3$).

Example 9c

Synthesis of 1,4-dihydrophenonthroline-4-one-3-carboxylic acid (1,4-DPCA) (3)

3 was prepared using a modified protocol described previously. 2 (2.00 g, 7.46 mmol) was combined with 40 mL 10% (w/v) KOH and refluxed (110° C.) for 1 hour, allowed to cool to room temperature, and residual diphenyl ether extracted using 28 mL petroleum ether (b.p. 80-110° C.). The product was precipitated with 40 mL 10% (w/v) HCl, filtered, washed with dH$_2$O and dried under high vacuum overnight to afford 3 (1.65 g, 6.87 mmol, 92%) as a beige powder. $^1$H NMR spectrum (500 MHz, DMSO-d$_6$), δ, ppm (J, Hz): 15.44 (1H, s, OH); 13.85 (1H, s, NH); 9.16 (1H, dd, $^3J_{2,3}$=4.3, $^3J_{2,4}$=1.6, H-2); 8.73 (1H, s, H-8); 8.64 (1H, dd, $^3J_{4,3}$=8.3, $^4J_{4,2}$=1.6, H-4); 8.26 (1H, d, $^3J_{6,5}$=8.8, H-6); 8.04 (1H, d, $^3J_{5,6}$=8.8, H-5); 7.92 (1H, dd, $^3J_{3,4}$=8.3, $^3J_{3,2}$=4.3, CH, k). Mass spectrum, m/z ($I_{rel}$, %): 241.1 [MH]+ (18), 263.0 (100), 279.0 (30), 503.1 (41). Purity was estimated as 99.8% by HPLC ($C_{18}$, 10 μm, 4.6×250 mm, 300 Å pores, silica; 2-100%, 30 min, acetonitrile gradient, 0.1% TFA; elution time=18.5 minutes; UV-vis, $\lambda_{max}$, nm: 261, 316, 331, 346).

Example 10

With reference to FIG. 2, a hydrogel carrier component and precursors thereto are described in Examples 10a-c. Various other hydrogel carriers and precursors, in accordance with this invention are described in co-pending application Ser. No. 13/798,744 filed Mar. 13, 2013, or as would otherwise be understood by those skilled in the art made aware of this invention through straight forward modifications of the synthetic techniques described therein—such application incorporated herein by reference in its entirety.

Example 10a

Synthesis of Glutaric Acid Terminated 8 Arm PEG (P8G).

Glutaric acid terminated PEG was synthesized as described previously. Briefly, 8-arm PEG-OH (19.4 g, 7.74 mmol OH) and glutaric anhydride (4.49 g, 38.7 mmol) were dissolved in chloroform (20 mL). Pyridine (3.12 mL, 38.7 mmol) was added dropwise, and the reaction mixture was refluxed at 82° C. for 24 hours under inert air. The product was precipitated with cold diethyl ether (200 mL) and spun down. The supernatant was decanted and the product re-dissolved in MeOH (200 mL). After incubation at −20° C. for 1 hour, the precipitate was centrifuged at −5° C. The supernatant was discarded, and the MeOH wash procedure was repeated twice more. Following cold diethyl ether precipitations (400 mL), the product was collected and dried under high vacuum overnight to afford a white powder (92% yield, 100% conversion). 1H NMR (500 MHz, Chloroform-d), δ, ppm: 4.24 (16H, t, terminal PEG CH2), 3.64 (1823H, m, backbone PEG CH2), 2.43 (16H, t, H-2 of glutaric acid), 2.39 (16H, t, H-4 of glutaric acid), 1.96 (16H, p, H-3 of glutaric acid).

Example 10b

Synthesis of N-Hydroxysuccinimide Terminated 8 Arm PEG (P8NHS).

NHS terminated 8 arm PEG was synthesized as described previously. P8G (18.6 g, 7.10 mmol COOH), NHS (8.18 g, 71.0 mmol) and EDC (13.6 g, 71.0 mmol) were dissolved in DMSO (47 mL). The solution was agitated for 30 minutes at room temperature, then it was diluted with MeOH (200 mL), precipitated at −20° C. for 1 hour, and spun down at −5° C. The supernatant was decanted, and the MeOH wash procedure was repeated twice more with 400 mL MeOH per wash. Following cold diethyl ether precipitations (400 mL), the product was dried under high vacuum to afford a white powder (95% yield, 96% conversion). 1H NMR (500 MHz, Chloroform-d), δ, ppm: 4.24 (16H, t, terminal PEG CH$_2$), 3.63 (1823H, m, backbone PEG CH$_2$), 2.84 (32H, m, NHS protons), 2.71 (16H, t, H-4 of glutaric acid), 2.49 (16H, t, H-2 of glutaric acid), 2.06 (16H, p, H-3 of glutaric acid).

Example 10c

Synthesis of Cysteine Terminated 8 Arm PEG (P8Cys).

Cysteine terminated 8 arm PEG was synthesized as described previously. PEG-NH$_2$ (20 g, 8.12 mmol NH$_2$) was dissolved in DMF (40 mL) after which DIEA was added dropwise (1.41 mL, 8.12 mmol). In a separate reaction vessel, Boc-Cys(Trt)-OH (15.0 g, 32.5 mmol) and BOP (14.4 g, 32.5 mmol) were dissolved in DMF (40 mL) and DIEA (5.65 mL, 32.5 mmol) was added dropwise. Both solutions were combined, and the coupling reaction was allowed to proceed at room temperature for 18 hours. Following precipitation in cold diethyl ether (400 mL), the product was re-dissolved in MeOH (40 mL) and precipitated in cold diethyl ether once more (400 mL). The cysteine was deprotected with TFA:TIS:EDT (300 mL, 95:2.5:2.5) cleavage solution at room temperature for 4 hours. TFA was evaporated under low pressure, and the product was precipitated in cold diethyl ether (400 mL). P8Cys was dissolved in MeOH (200 mL), precipitated at −20° C. overnight, and centrifuged at −5° C. The supernatant was decanted and the MeOH precipitation was repeated twice more using 100 mL MeOH per wash. Following diethyl ether precipitations (200 mL), the product was dried under high vacuum overnight to afford a white powder (73% yield, 84% endgroup conversion). 1H NMR (500 MHz, Acetic Acid-d4), δ, ppm: 4.41 (8H, t, α-C cysteine), 3.68 (1790H, m, backbone PEG CH2), 3.13 (16H, d, CH2 cysteine).

Example 11

Preparation of 1,4-DPCA/F127NF Crystals.

1.35 g Pluronic F127NF and 100 mg 1,4-DPCA were dissolved in 10 mL DMF. With stirring, the F127NF/1,4-DPCA solution was added dropwise to 500 mL ddH$_2$O at 60° C. The resulting crystals were collected by filtration and washed twice with 200 mL 0.27% (w/v) F127NF in ddH$_2$O. The crystals were re-suspended in 50 mL 0.27% (w/v) F127NF in ddH$_2$O and lyophilized to afford a white powder of F127NF/1,4-DPCA drug crystals (DCs). HPLC ($C_{18}$, 10 μm, 4.6×250 mm, 300 Å pores, silica; 2-100%, 30 min, acetonitrile gradient, 0.1% TFA; elution time=18.5 minutes) was used to quantify the drug content. The amount of 1,4-DPCA in the drug microcrystals showed batch to batch variation within the range of 35-53%.

Example 12

Filter Sterilization of PEG Polymers.

A 10% (w/v) solution of each PEG polymer in MeOH was filtered through a 0.2 μm filter into a sterile receptacle. The product was lyophilized to yield filter sterilized P8NHS or P8Cys.

Example 13

Formation of Drug-Loaded Hydrogels.

Separately, 10% (w/v) solutions of P8NHS and P8Cys were prepared in phosphate buffered saline (PBS) suspension of DCs at the desired drug concentration. The two polymer solutions were then mixed in a 1:1 v/v ratio and left undisturbed for 20 minutes to yield 70 μL cylindrical hydrogels (n=3).

Example 14

In-Vitro Drug Release from Hydrogels.

Each hydrogel cylinder prepared as described above was immersed in 5 mL PBS and at specified time points transferred into 5 mL of fresh PBS. UV/vis spectrophotometry was used to quantify drug release over time. The standard curve was prepared from stock solutions of known concentration of drug in DMSO. 10 of each stock solution was added to 990 μL PBS to yield a standard curve with 100-3000 ng/mL of drug. A PowerWave XS2 microplate spectrophotometer (Biotek Instruments, Inc., Winooski, Vt., USA) was used to quantify absorbance at 261 nm. Hydrogels without drug were used as negative controls.

Example 15

In-Vivo Hydrogel Injection.

Mice were injected subcutaneously at the base of the neck with 100 μL of 10% (w/v) 1:1 (w/w) ratio of P8Cys (with or without 1,4-DPCA drug crystal) to P8NHS hydrogel prepared in PBS. Each component was kept cold and mixed just prior to injection. At different time points, mice were euthanized and tissues were removed for protein and RNA analysis.

Example 16

Gelation Kinetics.

Gelation time was quantified using a previously described protocol. Briefly, the drug microcrystals were suspended in PBS and used to prepare 10% (w/v) P8NHS and 10% (w/v) P8Cys. The two polymer solutions were then mixed in a 1:1 (v/v) ratio and pipetted up and down using a standard 0.1-10 μL pipette tip. The time at which the material blocked the pipette tip was designated as the gelation time. Temperature was controlled at 37° C. through the use of a water bath.

Example 17

Cell Viability.

Viability of 3T3 fibroblasts exposed to drug microcrystals was quantified using ISO 10993. Briefly, different dilutions of drug microcrystals in cell culture medium were added to a subconfluent monolayer of 3T3 fibroblasts (n=3). The cells were cultured for 24 hours at 37° C., 5% $CO_2$, and >90% RH and then washed with PBS. Neutral red solution (0.4%) in DMEM was added, and the cells were stained for 3 hours. Following removal of the staining solution and washing the cells with PBS, the cells were destained using 50% ethanol, 49% dd$H_2O$ and 1% glacial acetic acid. Following 10 minutes of agitation, absorbance was measured at 540 nm and used to quantify cell viability. SDS was used as a positive control as specified by ISO 10993, and the $IC_{50}$ was found to be in the acceptable range of values hence confirming the validity of the assay. Culture medium was used as a negative control. Cell culture medium consisted of high glucose DMEM substituted with L-glutamine, penicillin/streptomycin, 10% v/v newborn calf serum and 20 mM HEPES.

Example 18

Figure 8A:
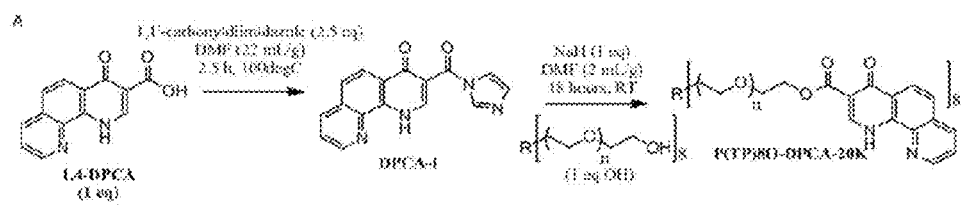
FIGS. 8A-B. (A) Synthetic scheme for preparing PEG DPCA or P(TP)8DPCA 20K. (B) The amount of 1,4 DPCA remaining bound to the PEG polymer over time when incubated in pH 7.4 buffer at 37° C.
Figure 8B:
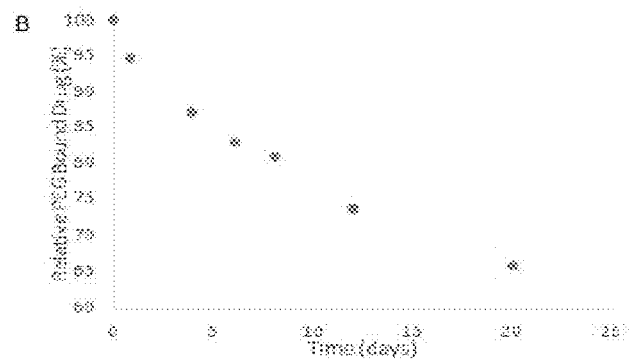

As an alternative to the drug conjugate of Example 11, 1,4-DPCA was coupled to 8 arm PEG to provide another route to or system for delivery (see FIG. 8A and Examples 18a-b). The drug was released via ester hydrolysis with approximately 35% hydrolysis over a 20 day period (see FIG. 8B and Example 18c).

Example 18a

Synthesis of DPCA-I.

1,4-DPCA (1 g, 4.163 mmol) was mixed with 22.2 mL DMF and stirred for a few minutes at room temperature. 1,1'-carbonyldiimidazole (1.69 g, 10.408 mmol) was added to the mixture with heating at 100° C. for 2.5 hours. The rxn vessel was removed from heat and allowed to reach room temperature. The precipitate was collected by filtration and washed twice with 10 mL chloroform. The product was dried under high vacuum to yield 1.169 g DPCA-I (96.7%) with approximately 96.2% activation/purity. $^1$H NMR (500 MHz, DMSO-d6, ref=2.50), δ, ppm: 13.201 (1H, s, a), 9.137 (1H, dd, l), 8.611 (1H, dd, j), 8.438 (1H, s, b), 8.231 (1H, d, h), 8.219 (1H, s, p), 7.955 (1H, d, i), 7.880 (1H, dd, k), 7.671 (1H, dd, n), 7.062 (1H, dd, o).

Example 18b

Synthesis of P(TP)8DPCA-20K.

Eight arm polyethylene glycol (P(TP)8OH-20K) (1 g, 0.369 mmol OH, 20 kDa, tripentaerythritol core, JenKem) was dissolved in 4 mL DMF, using a heat gun to help dissolve the polymer. The reaction vessel was purged with argon, and NaH was added (8.85 mg, 0.369 mmol), with stirring under argon at room temperature for ~30 minutes until effervescence ceased. DPCA-I (107 mg, 0.369 mmol) was added and stirred under argon at room temperature for 18 hours. PEG-$(NH_2)_2$-2K (369 mg, 0.369 mmol, 2 kDa, JenKem) was added and stirred for 30 minutes. The product was precipitated with 40 mL cold $Et_2O$, spun (4500 RCF, −5° C., 5 min), followed by decanting of the supernatant. Residual ether was removed with $N_2$, and the product was redissoved in 20 mL MeOH. After cooling at −20° C. for 30 minutes, the precipitate was spun down (4500 RCF, −5° C., 5 min), and the supernatant decanted. Methanol precipitation was repeated twice using 40 mL MeOH each time, with cooling at −20° C. for 45 minutes instead of 30. The precipitate was redissoved by hand-warming, then reprecipitated with 60 mL cold ether. The product was spun down and the supernatant was decanted. The product was washed with 30 mL ether and dried on high vacuum to yield 992 mg (91.3%) P(TP)8DPCA-20K with 38% end group activation (i.e. 3 of the 8 OH groups were activated with DPCA). $^1$H NMR (500 MHz, DMSO-d6, ref=2.50), δ, ppm: 9.110 (3H, dd, l), 8.583 (3H, dd, j), 8.573 (3H, s, b), 8.245 (3H, d, h), 7.909 (3H, d, i), 7.854 (3H, dd, k), 4.327 (6H, t, t), 3.512 (1969H, m, q+r+s).

Example 18c

Drug Release from PEG.

A solution of 1% w/v P(TP)8DPCA-20K was prepared in pH 7.4 buffer and 1 mL aliquots were made. The polymer solution was incubated at 37° C., and at various time points, an aliquot was lyophilized. The dried material was redissolved in DMSO and NMR was used to quantify ester hydrolysis (spectra not shown).

Example 19

While Examples 11 and 18 illustrate several drug conjugates in accordance with certain non-limiting embodiments of this invention, various other conjugates are contemplated, including those compounds comprising 1,4-DPCA coupled to any of the polyol-poly(alkylene oxide) macromolecules described in the aforementioned incorporated, co-pending '744 application. Likewise, various other compounds or compositions comprising other therapeutic agents of the sort described herein can be prepared or formulated using one or more such macromolecules, hydrogels and/or hydrogel precursor components.

While this invention has been described in conjunction with various macromolecules, hydrogels and/or hydrogel precursor components, it should be understood that these descriptions are provided only by way of example and are not intended to limit, in any way, the scope of this invention. For instance, without limitation, the compounds, compositions, methods and/or delivery systems of the present invention can be considered in the context of various other macromolecules, hydrogels and/or hydrogel precursors comprising a range of alkylene oxide polymer and/or copolymer components, such macromolecules, hydrogels and hydrogel precursors as are described in the aforementioned incorporated co-pending '744 application or as would otherwise be understood by those skilled in the art as commercially or otherwise available using synthetic techniques of the sort described therein or straight-forward modifications thereof.

Throughout this specification, the words "comprise", "comprises", and "comprising" are to be interpreted inclusively rather than exclusively. The words "consist", "consisting", and its variants, are to be interpreted exclusively, rather than inclusively. It should be understood that while various embodiments in the specification are presented using "comprising" language, under various circumstances, a related embodiment is also be described using "consisting of" or "consisting essentially of" language. It is to be noted that the term "a" or "an", refers to one or more, for example, "a drug," is understood to represent one or more drugs. As such, the terms "a" (or "an"), "one or more," and "at least one" are used interchangeably herein.

As used herein, the term "about" means a variability of 10% from the reference given, unless otherwise specified.

Unless defined otherwise in this specification, technical and scientific terms used herein have the same meaning as commonly understood by one of ordinary skill in the art to which this invention belongs and by reference to published texts, which provide one skilled in the art with a general guide to many of the terms used in the present application.

We claim:

1. A method of modulating proline hydroxylase activity, said method comprising:
providing a composition comprising a prodrug of 1,4-dihydrophenonthrolin-4-one-3-carboxylic acid (1,4-DPCA), said prodrug comprising a 1,4-DPCA component coupled to a cleavable polymer component, and a carrier component comprising a hydrogel comprising a chemical ligation product of

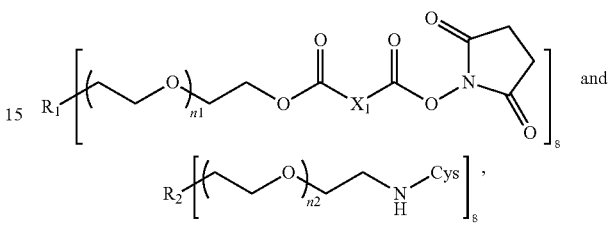

and wherein each of $R_1$ and $R_2$ is independently selected from hexaglycolic and tripentaerythritolic moieties, each of n1 and n2 is an integer independently selected from 1 to about 201, and Cys is an N-terminal cysteine residue; and
contacting said 1,4-DPCA component of said prodrug with a cellular medium expressing a proline hydroxylase, said cellular medium within a non-regenerative mammal presenting a tissue injury, said 1,4-DPCA component in an amount sufficient to modulate proline hydroxylase activity in said cellular medium and thereby induce a regenerative response.

2. The method of claim 1 wherein said contact comprises administration of said composition, said administration selected from oral intake and subcutaneous, intramuscular, intravenous and intraperitoneal injection.

3. The method of claim 2 wherein said administration comprises multiple doses over time.

4. The method of claim 2 wherein said administration is at a site distal to said tissue injury.

* * * * *